United States Patent
Abousy et al.

(10) Patent No.: US 10,410,308 B2
(45) Date of Patent: Sep. 10, 2019

(54) SYSTEM, METHOD, AND DEVICE FOR PERSONAL MEDICAL CARE, INTELLIGENT ANALYSIS, AND DIAGNOSIS

(75) Inventors: Khalid Abousy, Mclean, VA (US); Hamed Sallam, North Mankato, MN (US); Sameh Abouissa, Springfield, VA (US)

(73) Assignee: FUZZMED, INC., Mclean, VA (US)

( * ) Notice: Subject to any disclaimer, the term of this patent is extended or adjusted under 35 U.S.C. 154(b) by 499 days.

(21) Appl. No.: 12/296,986

(22) PCT Filed: Apr. 16, 2007

(86) PCT No.: PCT/US2007/009349
§ 371 (c)(1),
(2), (4) Date: Oct. 13, 2008

(87) PCT Pub. No.: WO2007/120904
PCT Pub. Date: Oct. 25, 2007

(65) Prior Publication Data
US 2009/0177495 A1   Jul. 9, 2009

Related U.S. Application Data

(60) Provisional application No. 60/791,882, filed on Apr. 14, 2006.

(51) Int. Cl.
G06F 19/00       (2018.01)
G16H 50/20       (2018.01)
G06Q 50/24       (2012.01)

(52) U.S. Cl.
CPC ............. *G06Q 50/24* (2013.01); *G16H 50/20* (2018.01); *G06F 19/325* (2013.01)

(58) Field of Classification Search
CPC .................................................. G16H 50/20
(Continued)

(56) References Cited

U.S. PATENT DOCUMENTS 5,924,074 A      7/1999  Evans
6,039,688 A *    3/2000  Douglas et al. ............ 600/300
(Continued)

FOREIGN PATENT DOCUMENTS

WO     WO 01/26026 A2    4/2001

OTHER PUBLICATIONS

International Search Report dated Sep. 29, 2008 issued in PCT/US07/09349.

(Continued)

*Primary Examiner* — Sheetal R Paulson
(74) *Attorney, Agent, or Firm* — Greenblum & Bernstein, P.L.C.

(57) ABSTRACT

A system for personal medical care, intelligent analysis and diagnosis may include: at least one source of medical information; at least one source of personal medical data for at least one patient; and one or more servers, where the medical information and the personal medical data are accessible to the server(s). The server(s) may include: an artificial intelligence (AI) component for analyzing the personal medical data with the medical information and identifying at least one issue requiring follow-up by the patient or by at least one external authorized entity; and at least one real-time communication link for bi-directional communication with at least one external authorized entity.

43 Claims, 18 Drawing Sheets

(58) Field of Classification Search
  USPC ......................................................... 705/2–3
  See application file for complete search history.

(56) References Cited

U.S. PATENT DOCUMENTS

| | | | |
|---|---|---|---|
| 6,581,038 B1* | 6/2003 | Mahran | 705/3 |
| 6,802,810 B2 | 10/2004 | Ciarniello et al. | |
| 7,181,375 B2 | 2/2007 | Rao et al. | |
| 7,412,458 B2 | 8/2008 | Parmar | |
| 7,444,291 B1 | 10/2008 | Prasad et al. | |
| 2003/0225597 A1* | 12/2003 | Levine | 705/3 |
| 2004/0122702 A1* | 6/2004 | Sabol et al. | 705/2 |
| 2004/0122706 A1* | 6/2004 | Walker et al. | 705/2 |
| 2005/0010088 A1* | 1/2005 | Iliff | 600/300 |
| 2007/0175980 A1* | 8/2007 | Alsafadi | 235/380 |

OTHER PUBLICATIONS

Written Opinion of the International Search Report (PCT/ISA/237).
William Jackson, "VA Tests Medical Smart Cards", Government Computer News (Apr. 12, 1999) http://www.gnc.com.

* cited by examiner

SYSTEM, METHOD, AND DEVICE FOR PERSONAL MEDICAL CARE, INTELLIGENT ANALYSIS, AND DIAGNOSIS

BACKGROUND OF THE INVENTION

Field of the Invention

The present invention relates generally to an intelligent health care management system, and more particularly to a system, method and device for maintaining, updating, and intelligently analyzing patient information to provide diagnostic and therapeutic information.

Related Art

Physicians have long maintained a medical record for each patient. These medical records have conventionally resided at the physician's office in a records area. When a patient changes physicians, unfortunately, absent making a copy of the patient's medical records and transporting the copy to the next physician, there is no easy way to provide a new physician access to the patient's prior medical history.

Electronic medical records have been developed to help heath care providers in caring for their patients. Unfortunately, since no standards exist, compatibility, exchangeability and accessibility of medical information is not conventionally possible among health care providers.

Conventionally, there are many databases around the world with patients' medical records, stored and locked up in proprietary formats, in doctor's offices, hospitals, government agencies, or third party payer's warehouses that are not readily accessible to a patient, or the patient's current physician. While this medical information may be very useful in the management of the patient, there is no conventionally available method for the medical information to reach the entities that could help that patient (e.g., physician, hospital, public and provide entities, offices, and thirty party payers) in a timely fashion, as would be needed, particularly in the case of emergency patient care needs.

Efforts to attempt to bring standardization of medical records in a universal medical record form and electronic medical record systems have made access to medical information easier. However, the main problem of obtaining data when the physician, hospital, insurance company, or the patient needs it, in a timely fashion, has remained an obstacle. Most medical records are currently stored in a doctor's office, hospital, or a database that are not always accessible to the patient when the patient or patient's health care giver need the information.

While most records may be in a pbysician's office or a hospital, and some few medical records are stored in an electronic or digital medical record system, very few doctors, patients, hospitals, or insurance providers have access to these medical records in an urgent setting, especially if the patient is traveling, away from the patient's residence and normal health care provider.

Another problem with conventional electronic medical records is that conventional medical record databases are generally redundant and incomplete. Updating and maintaining the databases is labor intensive and usually the database serves certain designated purposes for which it was programmed rather than being a complete medical record for the patient. For example a hospital may contain several databases for a patient's medical records, one designed for accounting/billing, another relating to recording patient symptoms, and others for laboratory results, for example.

Current physicians' lack of access to a patient's past medical records is a leading challenge in treating patients referred for care by a consultant. Quite often the patient's medical record is in the primary care provider's office and is thus inaccessible to the current physician handling the referral. For numerous reasons, such as office closings or inability to locate the chart in a timely manner, duplicate testing, and diagnosis may occur as a result of lack of access to critical medical information of the patient. Repetitive testing may often be performed, particularly in the case of urgent therapy, where lack of access to this information may be most critical, such as, for preoperative surgical clearance.

Access to information is also hindered by the fact that even when having access to pertinent medical information, the sheer volume of information in conventional records makes cumbersome the access of critical information from medical records. A better way of obtaining summarized, merged, up to date information about a patient is not available to a patient or the patient's health care providers, using conventional systems.

Further, since the drafting of the Medicare Prescription Drug, Improvement, and Modernization Act of 2003, prescription error reduction has become one of the important mandates for the medical industry as well as for the government and private health care sectors to improve health care delivery. Also, laboratory results frequently require changing of the medication regimens to avoid potential toxicities, drug interactions and side effects for the patients. The dispersion of a patient's medical records can make it difficult to identify and correct such potential undesirable drug interactions. Even in cases where all of the relevant records are co-located, a physician or pharmacist may still miss the potentially harmful interactions.

Further, the distribution and inaccessibility of a patient's whole health and medical record, combined with limited time for office visits, may prevent a treating health care provider from being able to identify secondary issues that may aid in diagnosis and treatment.

What is needed is a system, method, and computer program product which may be adapted to provide a patient a portable, digital medical record, which may be carried by the patient so access to the patient's medical information will always be available. This previously unfulfilled need is particularly in demand in emergency situations, when a health care provider has only a limited time to diagnose an illness and provide care for a patient, in life threatening peril.

SUMMARY OF THE INVENTION

In an exemplary embodiment of the present invention a system, method and computer program product for providing patient access to or control of the patient's medical record is disclosed. A flexible, portable, patient-controlled system for storing, maintaining, and processing medical information may be provided.

In an exemplary embodiment, a system may include: at least one source of medical information; at least one source of personal medical data for at least one patient; and at least one server, wherein the medical information and the personal medical data are accessible to the at least one server, the at least one server including: an artificial intelligence (AI) component for analyzing the personal medical data with the medical information and identifying at least one issue requiring follow-up by the patient or by at least one external authorized entity; and at least one real-time communication link for bi-directional communication with at least one external authorized entity. The personal medical data for at least one patient may be accessible to the at least one patient. The at least one real-time communication link uses the Health Level 7 protocol.

The AI component may include: an AI conduction component; and an AI derivation component. The AI derivation component may include a diagnosis protocol; a therapy protocol; and an inference engine. The AI derivation component may create the diagnosis and therapy protocols using information from the at least one source of medical information. The AI component identifies at least one of: a potential drug interaction; a potential side effect; a potential drug toxicity; a suggested medical test to be performed; an allergic reaction; a prior condition before a medical procedure is performed; a clinical decision; a recommendation for treatment; a recommendation for management; a recommendation for therapy; a diagnosis; or a procedure of interest to a health care monitoring agency. The AI component may include at least one of: fuzzy logic; artificial intelligence (AI); a knowledge base (KB); a neural network; a decision support system (DSS); an agent; a software agent; or an expert system.

The system may further include: a data management engine to organize, store, edit, maintain, format, and process data from the personal medical data and from the medical information.

The at least one source of medical information may include at least one of: a standard medical guideline; a pharmaceutical guideline; a government regulatory guideline; a health preventative guideline; a medical condition description; an insurance guideline; a medical journal; a research report; International Classification of Diseases (ICD) code; Current Procedural Terminology (CPT) codes; or a consensus medical committee guideline.

The at least one source of personal medical data may include at least one of: patient medical records, including: physician records, vaccine records, dental records, cardiac records, pharmaceutical records, laboratory records, radiological records; advance directives; do not resuscitate (DNR) orders; living wills; organ donation designations; scanned medical records; indexed medical information; textual medical record information; image information; streamed data; video data; audio data; handwritten notes; dictation; insurance information; prescription information; drug interaction information; allergy information; optical character recognition (OCR) data; recognized data; voice recognition data; or captured data.

The medical information and the personal medical data may be accessible to the at least one server or the at least one patient for doing at least one of: communicating; replicating; synchronizing; reading, writing, storing, retrieving, editing, modifying, adding to, updating, deleting, inserting, uploading, data mining, downloading, transferring, emailing, scheduling, notifying, alerting, text messaging, or instant messaging the medical information and the personal medical data.

The at least one external authorized entity may include at least one of: a health insurance provider, a pharmacy, a hospital, an urgent care facility, a health clinic, a physician, a physician's office, a nurse, a physician's assistant, a federal agency, a state agency, a regulatory agency, an emergency medical service, an outpatient clinic, an outpatient diagnostic clinic, a medical laboratory, the patient, or another entity authorized by the patient.

The system may further include: a client personal medical device comprising: a storage medium for storing the personal medical data for the at least one patient; and a communication interface for communicating with the system as one of the at least one external authorized entities. The client personal medical device may include a graphical user interface (GUI) adapted to access the personal medical data; wherein the GUI is operative on at least one of: a display on the client device, or a computer. The client personal medical device may include a display adapted to display at least one of the personal medical data or analyzed medical data.

The personal medical device may include at least one of: a computing device; a communications device; a storage device comprising at least one of: a hard drive, a universal serial bus (USB) device, a flash memory device, a memory device, a magnetic device, an optical, a magneto-optical (MO), a compact disk (CD), a radio frequency identification device (RFID), a passive device, an active device, or a chip; a card; a smartcard; a telephony device; personal digital assistant (PDA); a handheld device; a portable device; a wireless device; or a networked device.

The storage medium may include at least one of: a hard disk; a universal serial bus (USB) storage medium; a flash memory medium; a non-volatile memory medium; memory; a magnetic medium; an optical medium; a magneto-optical (MO) medium; a compact disk (CD) medium; a digital versatile disk (DVD) medium; CD-R medium; a DVD-R medium; a radio frequency identification (RFID) medium; a passive medium; an active medium; or a medium comprising a chip.

The personal medical device further may include an intelligent analysis device including at least one of: means for suggesting improved care; means for suggesting improved management; means for filtering the personal medical information; means for providing a pre-operative assessment; means for providing suggestions; means for providing analyzed information comprising at least one of health, insurance or personal information; means for providing analyzed information comprising at least one of health insurance, civil or government entities; means of analyzing data comprising medical conditions listed within or outside the ICD & CPT domains; means for analyzing data comprising at least one of: genetics, hypercholesteremia, hypertension, diabetes, smoking or obesity; means of generating a medical health profile comprising the patients medical conditions; means for generating a cardiovascular health profile comprising means for tracking at least one of: patient weight, blood pressure; cholesterol profile, blood sugar level, or glycocylated hemoglobin level; means for providing a portal for medical information comprising means for linking at least one of: healthcare provider, hospital, insurance provider, physicians, civil and government entities; means for providing organ system checkups comprising at least one of: thyroid tests, prostate specific antigen, mammography, colonoscopy examination, pelvic exams, chest x-rays, dexa bone scan, cell blood counts, chemistries, or vaccinations; means for at least one of: reducing a need for repeat testing, or avoiding unnecessary testing; means for formulating a diagnosis; or means for retrieving pertinent medical data in a timely fashion.

The system may further include: a user interface for allowing the patient or the at least one external authorized entity to read, write, store, retrieve, edit, modify, add to, update, delete, insert, upload, data mine, download, transfer, email, schedule, notify, alert, text message, or instant message the medical information and the personal medical data. The user interface may include a medical adviser component.

The system may further include an electronic health record and an electronic medical record.

The system may further include an alert generator for generating and sending an alert to at least one of the patient or the at least one external authorized entity regarding the identified issue.

In another exemplary embodiment, a technique may include receiving data about a patient from an external health care entity in a medical center system; storing the received data in a patient medical data database (PMDB); intelligently analyzing the data according to medical information; identifying at least one issue requiring follow-up by at least one external authorized entity; and communicating the at least one issue to at least one external authorized entity.

The technique may further include retrieving the stored patient data in an artificial intelligence (AI) conduction component; and converting the retrieved data to a first format. Converting the retrieved data may include "fuzzifying" the data.

The technique may further include: pre-processing the received data in prior to storing the data in the PMDB, including at least one of: synchronizing, organizing, maintaining, editing, or processing the received data.

Intelligently analyzing may include at least one of: deriving a diagnosis protocol; deriving a therapy protocol; querying and retrieving data from at least one of standard medical guideline data, physician recommendations, intelligent rules from medical experts; and using at least one of fuzzy logic; artificial intelligence (AI); a knowledge base (KB); a neural network; providing a decision support system (DSS); providing agent; providing software agent; or providing an expert system.

The technique may further include maintaining a medical decision database; and updating the medical decision database with the identified at least one issue.

The technique may further include alerting at least one of: the patient, a health care provider of the patient, or an external authorized entity of the identified at least one issue.

The technique may further include communicating the at least one issue to a plurality of external authorized entities. The technique may further include for each of the plurality of external authorized entities, communicating a message regarding the at least one issue, wherein the message is specific to the each of the plurality of external authorized entities.

In another exemplary embodiment, a technique may include: receiving or placing medical data on a personal medical device; analyzing the medical data with intelligence; formatting the analyzed medical data according to the intelligence; and storing the formatted medical data.

The receiving medical data may include at least one of: scanning the medical data; imaging the medical data; capturing the medical data; accessing the medical data; displaying the medical data; processing the medical data; indexing the medical data; archiving the medical data; backing up the medical data; updating the medical data; providing the medical data; storing the medical data; capturing ECG data; capturing textual data; capturing image data; capturing streamed data; capturing video data; capturing audio data; capturing handwritten notes; capturing dictation; capturing insurance information; capturing prescription information; capturing drug interaction information; capturing allergy information; scanning optical character recognition (OCR) data; recognizing data; using voice recognition data; or capturing metadata about the medical data.

The medical data may include at least one of: patient medical records; medical records comprising at least one of: doctor records, vaccine records, dental records, or cardiac records; scanned medical records; indexed medical information; textual information; image information; streamed data; video data; audio data; handwritten notes; dictation; insurance information; prescription information; drug interaction information; allergy information; optical character recognition (OCR) data; recognized data; voice recognition data; or captured data.

The placing of medical data may include at least one of: storing the medical data on the personal medical information device; storing the medical data on a storage device; or placing the medical data on a storage medium.

The intelligence may include at least one of: providing fuzzy logic; providing artificial intelligence (AI); providing a knowledge base (KB); providing a neural network; providing a decision support system (DSS); providing agent; providing software agent; or providing an expert system.

The personal medical information device may include at least one of: a computing device; a communications device; a storage device comprising at least one of: a hard drive, a universal serial bus (USB) device, a flash memory device, a memory device, a magnetic device, an optical, a magneto-optical (MO), a compact disk (CD), a radio frequency identification device (RFID), a passive device, an active device, or a chip; a card; a smartcard; a telephony device; personal digital assistant (PDA); a handheld device; a portable device; a wireless device; or a networked device.

Storing on the storage device may include storing on at least one of: a computing device; a communications device; a storage device comprising at least one of: a hard drive, a universal serial bus (USB) device, a flash memory device, a memory device, a magnetic device, an optical, a magneto-optical (MO), a compact disk (CD), a radio frequency identification device (RFID), a passive device, an active device, or a chip; a card; a smartcard; a telephony device; personal digital assistant (PDA); a handheld device; a portable device; a wireless device; or a networked device.

Analyzing the medical data may include at least one of: suggesting improved care; suggesting improved management; filtering the personal medical information; providing a pre-operative assessment; providing suggestions; providing analyzed information comprising at least one of health, insurance or personal; analyzing data comprising at least one of: genetics, hypercholesteremia, hypertension, diabetes, smoking or obesity; generating a cardiovascular health profile comprising means for tracking at least one of: patient weight, blood pressure; cholesterol profile, blood sugar level, or glycocylated hemoglobin level; providing organ system checkups comprising at least one of: thyroid tests, prostate specific antigen, mammography, colonoscopy examination, pelvic exams, chest x-rays, dexa bone scan, cell blood counts, chemistries, or vaccinations; reducing a need for repeat testing; avoiding unnecessary testing; formulating a diagnosis; or retrieving pertinent medical data in a timely fashion.

In another exemplary embodiment, the invention may be a portable personal medical device, including: a storage medium for storing personal medical data for a patient; and a communication interface for communicating with a centralized intelligent health care system.

The device may further include: a graphical user interface (GUI) adapted to access the personal medical data; wherein the GUI is operative on at least one of: a display on the client device, or a computer.

The device may further include: a display adapted to display at least one of the personal medical data or analyzed medical data.

The device may further include: at least one of: a computing device; a communications device; a storage device comprising at least one of: a hard drive, a universal serial bus (USB) device, a flash memory device, a memory device, a magnetic device, an optical, a magneto-optical (MO), a compact disk (CD), a radio frequency identification device (RFID), a passive device, an active device, or a chip; a card; a smartcard; a telephony device; personal digital assistant (PDA); a handheld device; a portable device; a wireless device; or a networked device.

The storage medium of the device may further include: at least one of: a hard disk; a universal serial bus (USB) storage medium; a flash memory medium; a non-volatile memory medium; memory; a magnetic medium; an optical medium; a magneto-optical (MO) medium; a compact disk (CD) medium; a digital versatile disk (DVD) medium; CD-R medium; a DVD-R medium; a radio frequency identification (RFID) medium; a passive medium; an active medium; or a medium comprising a chip.

The device may further include: an intelligent analysis device including at least one of: means for suggesting improved care; means for suggesting improved management; means for filtering the personal medical information; means for providing a pre-operative assessment; means for providing suggestions; means for providing analyzed information comprising at least one of health, insurance or personal information; means for providing analyzed information comprising at least one of health insurance, civil or government entities; means of analyzing data comprising medical conditions listed within or outside the ICD & CPT domains; means for analyzing data comprising at least one of: genetics, hypercholesteremia, hypertension, diabetes, smoking or obesity; means of generating a medical health profile comprising the patients medical conditions; means for generating a cardiovascular health profile comprising means for tracking at least one of: patient weight, blood pressure; cholesterol profile, blood sugar level, or glycocylated hemoglobin level; means for providing a portal for medical information comprising means for linking at least one of: healthcare provider, hospital, insurance provider, physicians, civil and government entities; means for providing organ system checkups comprising at least one of: thyroid tests, prostate specific antigen, mammography, colonoscopy examination, pelvic exams, chest x-rays, dexa bone scan, cell blood counts, chemistries, or vaccinations; means for at least one of: reducing a need for repeat testing, or avoiding unnecessary testing; means for formulating a diagnosis; or means for retrieving pertinent medical data in a timely fashion.

In an exemplary embodiment, the invention may further comprise a user interface adapted to access the personal medical data. In one aspect of the invention, the access may comprise at least one of read, write, store, retrieve, edit, modify, add to, update, delete, insert, upload, data mining, download, transfer, email, schedule, notify, alert, or instant message.

The invention may further comprise a display adapted to display at least one of the personal medical data or analyzed medical data.

In one aspect of the invention, the intelligence may be at least one of fuzzy logic, artificial intelligence (AI), a knowledge base (KB), a neural network, a decision support system (DSS), agent, software agent, or an expert system. In an exemplary aspect, the intelligence may be fuzzy logic.

In another embodiment, the personal medical data may include patient medical records or medical records, e.g., including doctor records, vaccine records, dental records, or cardiac records, or scanned medical records, indexed medical information, textual information, image information, streamed data, video data, audio data, handwritten notes, dictation, insurance information, prescription information, drug interaction information, allergy information, optical character recognition (OCR) data, recognized data, voice recognition data; or captured data. In another aspect, the storage device may be a storage medium.

In one aspect of the invention, the personal medical information device may comprise at least one of a computing device; a communications device; a storage device comprising at least one of a hard drive, a universal serial bus (USB) device, a flash memory device, a memory device, a magnetic device, an optical, a magneto-optical (MO), a compact disk (CD), a radio frequency identification device (RFID), a passive device, an active device, or a chip; a card; a smartcard; a telephony device; personal digital assistant (PDA); a handheld device; a portable device; a wireless device; or a networked device. In another aspect, the storage medium may comprise at least one of a hard disk; a universal serial bus (USB) storage medium; a flash memory medium; a non-volatile memory medium; memory; a magnetic medium; an optical medium; a magneto-optical (MO) medium; a compact disk (CD) medium; a digital versatile disk (DVD) medium; CD-R medium; DVD-R medium; a radio frequency identification (RFID) medium; a passive medium; an active medium; or a medium comprising a chip.

In another exemplary embodiment, the analysis device may comprise at least one of: means for suggesting improved care; means for suggesting improved management; means for filtering said personal medical information; means for providing a pre-operative assessment; means for providing suggestions; means for providing analyzed information comprising at least one of health, insurance or personal; means for analyzing data comprising at least one of: genetics, hypercholesteremia, hypertension, diabetes, smoking or obesity; means for generating a cardiovascular health profile comprising means for tracking at least one of: patient weight, blood pressure; cholesterol profile, blood sugar level, or glycocylated hemoglobin level; means for providing organ system checkups comprising at least one of: thyroid tests, prostate specific antigen, mammography, colonoscopy examination, pelvic exams, chest x-rays, dexa bone scan, cell blood counts, chemistries, or vaccinations; means for at least one of: reducing a need for repeat testing, or avoiding unnecessary testing; means for formulating a diagnosis; or means for retrieving pertinent medical data in a timely fashion.

In another embodiment, the present invention may relate to a method comprising: receiving medical data; placing medical data on a personal medical information device; and analyzing said personal medical data with intelligence. In one aspect, the receiving medical data may comprise at least one of: scanning said medical data; imaging said medical data; capturing said medical data; accessing said medical data; displaying said medical data; processing said medical data; indexing said medical data; archiving said medical data; backing up said medical data; updating said medical data; providing said medical data; storing said medical data; capturing ECG data; capturing textual data; capturing image data; capturing streamed data; capturing video data; capturing audio data; capturing handwritten notes; capturing dictation; capturing insurance information; capturing prescription information; capturing drug interaction information; capturing allergy information; scanning optical character recognition (OCR) data; recognizing data; using voice recognition data; or capturing metadata about said medical data.

In another aspect, the medical data may comprise at least one of: patient medical records; medical records comprising at least one of: doctor records, vaccine records, dental records, or cardiac records; scanned medical records; indexed medical information; textual information; image information; streamed data; video data; audio data; handwritten notes; dictation; insurance information; prescription information; drug interaction information; allergy information; optical character recognition (OCR) data; recognized data; voice recognition data; or captured data.

In yet another aspect, the placing medical data may comprise at least one of: storing said medical data on said personal medical information device; storing said medical data on a storage device; or placing said medical data on a storage medium.

In a further aspect, the intelligence may comprise at least one of: providing fuzzy logic; providing artificial intelligence (AI); providing a knowledge base (KB); providing a neural network; providing a decision support system (DSS); providing agent; providing software agent; or providing an expert system. The intelligence may comprise fuzzy logic.

The personal medical information device may comprise at least one of: a computing device; a communications device; a storage device comprising at least one of: a hard drive, a universal serial bus (USB) device, a flash memory device, a memory device, a magnetic device, an optical, a magneto-optical (MO), a compact disk (CD), a radio frequency identification device (RFID), a passive device, an active device, or a chip; a card; a smartcard; a telephony device; a personal digital assistant (PDA); a handheld device; a portable device; a wireless device; or a networked device.

In another aspect of the invention, the storing on said storage medium may comprise storing on said storage medium comprising at least one of: a hard disk; a universal serial bus (USB) storage medium; a flash memory medium; a non-volatile memory medium; memory; a magnetic medium; an optical medium; a magneto-optical (MO) medium; a compact disk (CD) medium; a digital versatile disk (DVD) medium; CD-R medium; DVD-R medium; a radio frequency identification (RFID) medium; a passive medium; an active medium; or a medium comprising a chip.

In an another aspect, the storage device may comprise storing on at least one of: a computing device; a communications device; a storage device comprising at least one of: a hard drive, a universal serial bus (USB) device, a flash memory device, a memory device, a magnetic device, an optical, a magneto-optical (MO), a compact disk (CD), a radio frequency identification device (RFID), a passive device, an active device, or a chip; a card; a smartcard; a telephony device; personal digital assistant (PDA); a handheld device; a portable device; a wireless device; or a networked device.

In a further aspect, the analyzing of the medical data may comprise at least one of: suggesting improved care; suggesting improved management; filtering said personal medical information; providing a pre-operative assessment; providing suggestions; providing analyzed information comprising at least one of health, insurance or personal; analyzing data comprising at least one of: genetics, hypercholesteremia, hypertension, diabetes, smoking or obesity; generating a cardiovascular health profile comprising means for tracking at least one of: patient weight, blood pressure; cholesterol profile, blood sugar level, or glycocylated hemoglobin level; providing organ system checkups comprising at least one of: thyroid tests, prostate specific antigen, mammography, colonoscopy examination, pelvic exams, chest x-rays, dexa bone scan, cell blood counts, chemistries, or vaccinations; reducing a need for repeat testing; avoiding unnecessary testing; formulating a diagnosis; or retrieving pertinent medical data in a timely fashion.

In another exemplary embodiment, the invention relates to a computer readable medium with program logic embodied thereon, wherein the program log which when executed on a computer enables performing a method comprising: receiving medical data; placing medical data on a personal medical information device; and analyzing said personal medical data with intelligence.

Further features and advantages of the invention, as well as the structure and operation of various embodiments of the invention, are described in detail below with reference to the accompanying drawings.

BRIEF DESCRIPTION OF THE DRAWINGS

The foregoing and other features and advantages of the invention will be apparent from the following, more particular description of exemplary embodiments of the invention, as illustrated in the accompanying drawings wherein like reference numbers generally indicate identical, functionally similar, or structurally similar elements. The left most digits in the corresponding reference number indicate the drawing in which an element first appears.

EXEMPLARY DEFINITIONS

Figure 1:
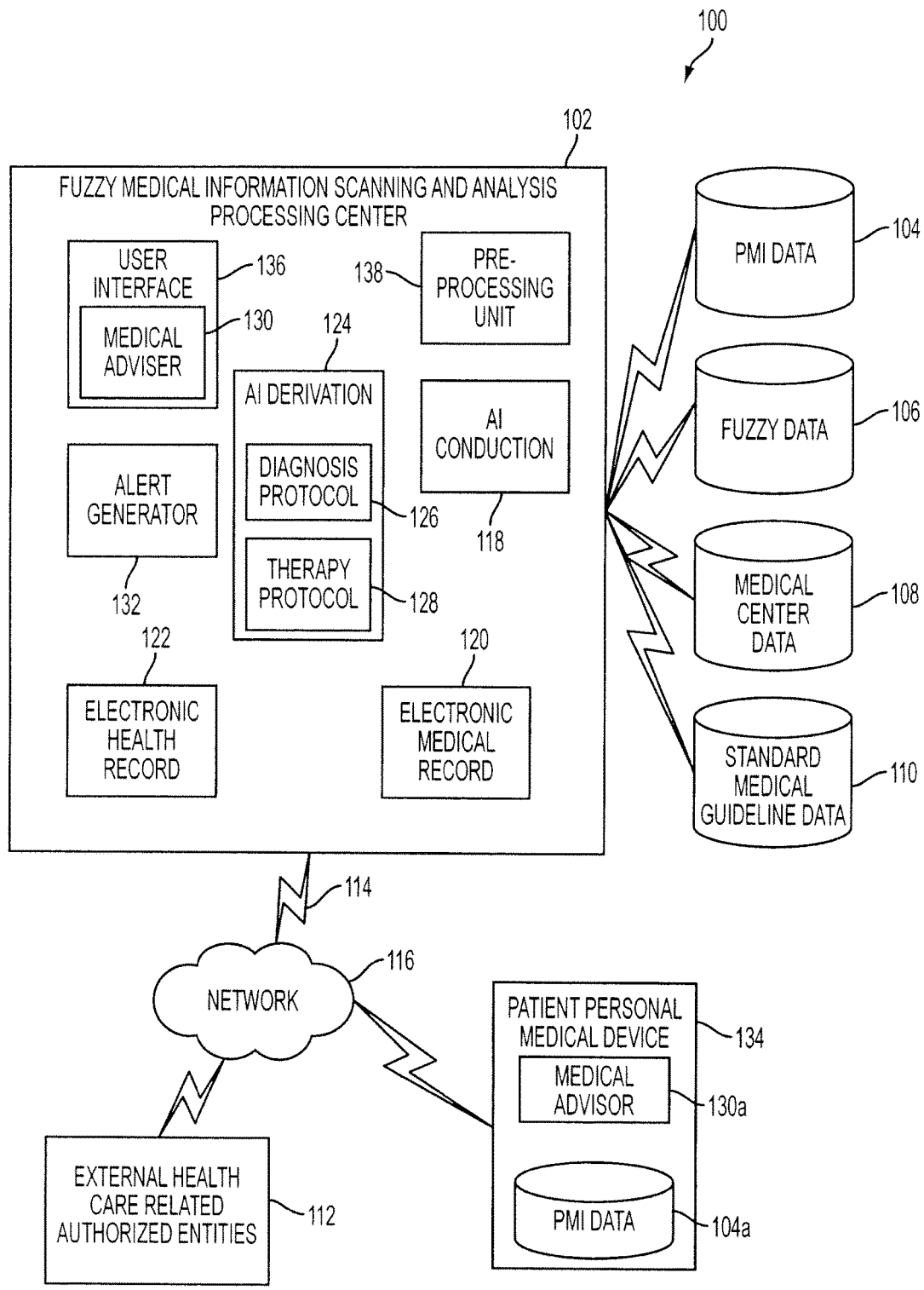
FIG. 1 depicts a block diagram of an exemplary embodiment of a system according to the present invention.

In describing the invention, the following definitions are applicable throughout (including above).

A "computer" may refer to one or more apparatus or one or more systems that are capable of accepting a structured input, processing the structured input according to prescribed rules, and producing results of the processing as output. Examples of a computer may include: a computer; a stationary or portable computer; a computer having a single processor, multiple processors, or multi-core processors, which may operate in parallel or not in parallel; a general purpose computer; a supercomputer; a mainframe; a super mini-computer; a mini-computer; a workstation; a microcomputer; a server; a client; an interactive television; a web appliance; a telecommunications device with internet access; a hybrid combination of a computer and an interactive television; a portable computer; a tablet personal computer (PC); a personal digital assistant (PDA); a portable telephone; application-specific hardware to emulate a computer or software, such as, for example, a digital signal processor (DSP), a field-programmable gate array (FPGA), an application specific integrated circuit (ASIC), an application specific instruction-set processor (ASIP), a chip, chips, or a chip set; a system-on-chip (SoC) or a multiprocessor system-on-chip (MPSoC); an optical computer; a quantum computer; a biological computer; and an apparatus that may accept data, may process data in accordance with one or more stored software programs, may generate results, and typically may include input, output, storage, arithmetic, logic, and control units.

"Software" may refer to prescribed rules to operate a computer or a portion of a computer. Examples of software may include: code segments; instructions; applets; pre-compiled code; compiled code; interpreted code; computer programs; and programmed logic.

A "computer-readable medium" may refer to any storage device used for storing data accessible by a computer. Examples of a computer-readable medium may include: a magnetic hard disk; a floppy disk; an optical disk, such as a CD-ROM and a DVD; a magnetic tape; a memory chip; or other types of media that can store machine-readable instructions thereon.

A "computer system" may refer to a system having one or more computers, where each computer may include a computer-readable medium embodying software to operate the computer. Examples of a computer system may include: a distributed computer system for processing information via computer systems linked by a network; two or more computer systems connected together via a network for transmitting or receiving information between the computer systems; and one or more apparatuses or one or more systems that may accept data, may process data in accordance with one or more stored software programs, may generate results, and typically may include input, output, storage, arithmetic, logic, and control units.

A "network" may refer to a number of computers and associated devices that may be connected by communication facilities. A network may involve permanent connections such as cables or temporary connections such as those that may be made through telephone or other communication links. A network may further include hard-wired connections (e.g., coaxial cable, twisted pair, optical fiber, waveguides, etc.) or wireless connections (e.g., radio frequency waveforms, free-space optical waveforms, acoustic waveforms, satellite transmissions, etc.). Examples of a network may include: an internet, such as the Internet; an intranet; a local area network (LAN); a wide area network (WAN); and a combination of networks, such as an internet and an intranet. Exemplary networks may operate with any of a number of protocols, such as Internet protocol (IP), asynchronous transfer mode (ATM), or synchronous optical network (SONET), user datagram protocol (UDP), IEEE 802.x, etc.

DETAILED DESCRIPTION OF EMBODIMENTS OF THE PRESENT INVENTION

An exemplary embodiment of the invention is discussed in detail below. While specific exemplary embodiments are discussed, it should be understood that this is done for illustration purposes only. A person skilled in the relevant art will recognize that other components and configurations can be used without parting from the spirit and scope of the invention.

Overview

Figure 28:
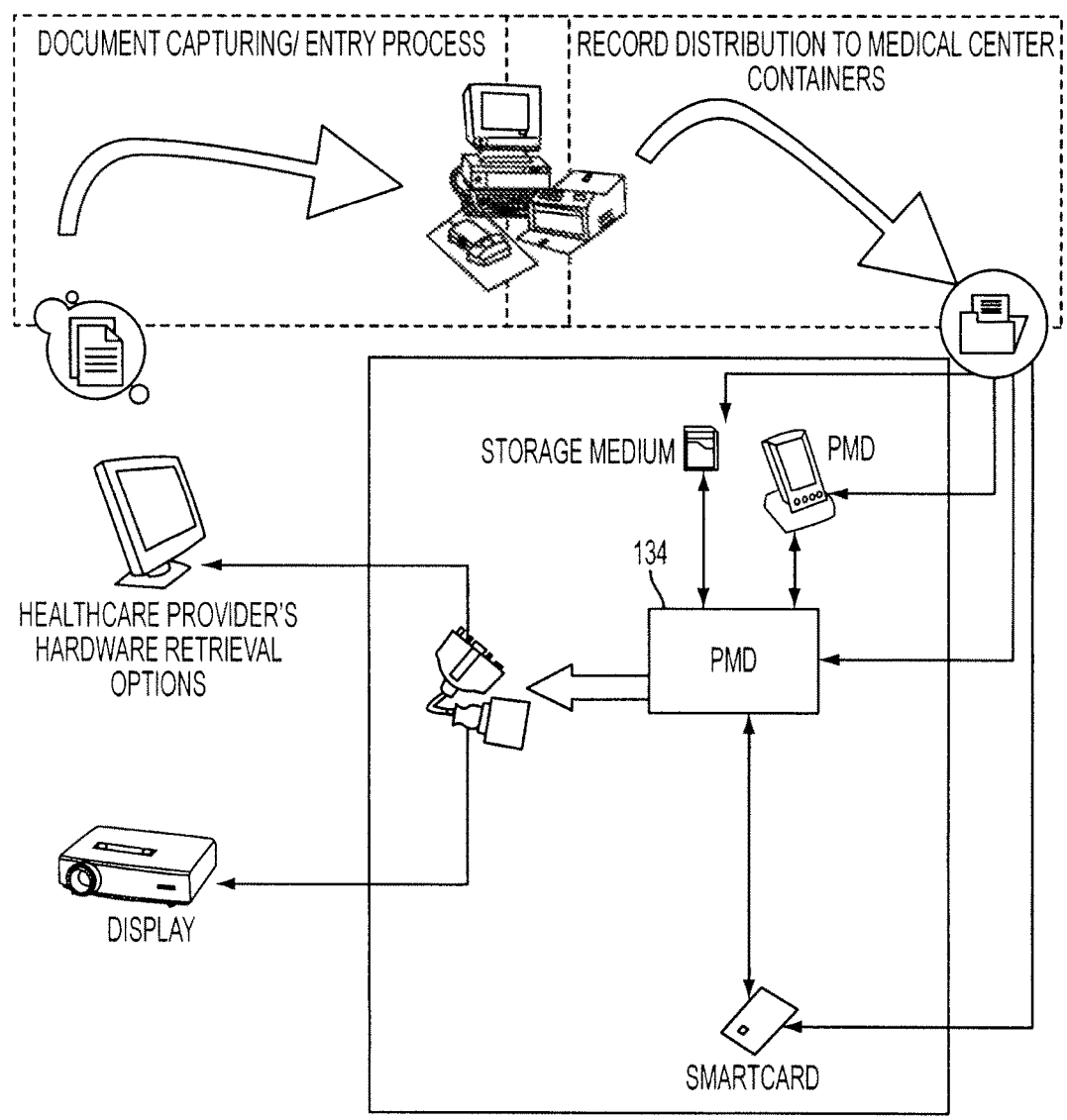
FIG. 28 depicts an exemplary hardware components for and a process of document capture and data entry according to embodiments of the present invention.

Exemplary embodiments of the present invention may provide a system and method for maintaining a centralized medical information scanning and analysis center and storage repository of patient medical information, which may be accessible and updateable in real-time to a variety of healthcare related entities. The system may store analyzed medical information on a personal medical information device which may be carried by a patient. The system and method may also provide one or more artificial intelligence (AI) processes for analyzing patient medical records and sources of medical knowledge, for example, to suggest diagnoses, treatment options, drug interactions, and other aspects of medical care, in real-time or in an archival manner, to the patient and health care entities. Embodiments of the present invention may include a personal device, (see, e.g., FIG. 28), carried by the patient, which may hold all of the patient's medical data for instantaneous retrieval by a health-care provider or entity, wherever the patient is. The device may be updated by the centralized medical information, scanning and analysis center, or externally, for example, at a physician's office. The device may alert the patient to possible drug interactions, or to suggestions for follow-up medical tests, in conjunction with the centralized system and artificial intelligence processes. The system may further include a user interface to facilitate retrieval of, updating of, and interaction with a patient's records. In an exemplary embodiment, the user interface may include fuzzy logic to provide timely information about the patient at the point of care.

Embodiments of the present invention may provide the following functionality. An embodiment may be the unifying domain for a national healthcare medical record system where any authorized entity involved in the health care delivery of a patient can use the information in the system for its resources. For example, embodiments of the invention may allow any doctor involved in the care of a patient to look up the patient's medical information. At the same time the patient may view his records, and his insurance provider can view the patient's medical record. Only domains involved in the care of the patient, and only under appropriate U.S. Health Insurance Portability and Accountability Act of 1996 (HIPAA) (or other national regulation for patient privacy and access to records) compliance, can have access to this particular patient's information.

Embodiments of the present invention may allow updating of a patient's medical record, and provide clinical suggestions based on any updated patient medical information. An embodiment may allow the patient, hospital, physician, insurance providers, and any related health care domain to access any pertinent information related to patient care in an online manner.

Embodiments of the present invention may reduce the time needed for insurance entities to pay the health care providing domains. Conventionally, medical bills are not charged until final chart compilation in a medical record department of the billing entity. By providing a real time and continuous feed to the exemplary system, payment processing and disbursement time may be cut significantly. In other words, through a health care standard, such as Health Level 7 (HL7) or other compatible solution, a hospital, for example, may provide information regarding the charges and diagnosis (e.g., appropriate international classification of diseases (ICD) codes or current procedural terminology (CPT) codes) to an exemplary system. Embodiments of the invention may then relay the information to the appropriate health care domain.

Embodiments of the present invention may allow a patient to monitor his own medical report. This will help the patients to do the following. Patients may compare their care to the accepted standard medical record guidelines. Patients may compare their medical condition with any disease process or population similar to their medical condition or any other comparison regarding any medical situation based on data, diagnosis and treatment protocols in an exemplary system. Patients may compare how their care is provided by a certain physician, hospital, or any related health domain compared to the national average or accepted practices. Patients may interact with any pertinent health care domains through an exemplary system to provide information regarding their medical situation.

Embodiments of the present invention may alert the patient, his primary care physician, as well as any health related monitoring agency that monitors health related demographics, e.g. information about a person such as e.g., age, sex, address, nationality, creed, ethnicity, etc., that he may not be on appropriate medications to treat his medical conditions.

Central System

As seen in the block diagram 100 in FIG. 1, embodiments of the present invention may include a centralized component, referred to hereinafter as the medical information scanning and analysis processing center 102, where medical information and patient data may be scanned, analyzed or stored, and where the primary artificial intelligence processes reside and take place. Medical information processing information processing center 102 may be physically centralized, or may be physically distributed and functionally centralized. Medical information processing center 102 may include and operate on one or more server computers. Medical information processing center 102 may be coupled to one or more databases, e.g. databases 104, 106, 108, and 110. The databases may be resident on the servers, or may be separate from and accessible to the server(s). Medical information processing center 102 may include a variety of network communication ports 114 for communicating with external entities 112, for example, through a network 116. For example, medical information processing center 102 may have Ethernet connections, cellular telephone connections, landline telephone connections, radio frequency connections, or other wired or wireless connections for transmitting and receiving data, as well as direct or indirect connection to scanning or indexing devices.

Medical information processing center 102 may include a pre-processing unit 136 may be software or hardware that organizes, maintains, edits, and processes the incoming patient data and medical information. The pre-processed data may be stored in the patient medical information database 104.

Medical information processing center 102 may include various artificial intelligence components, such as AI conduction component 118, and AI derivation component 124, which are discussed in greater detail below.

Medical information processing center 102 may further include electronic medical record 120 and electronic health record 122. EMR 120 may include data traditionally found on a patient's paper records, e.g. charts, health workers' notes, test results, progress notes. EHR 122 may include personal demographic data, address, ethnicity, number of hospitalizations, other statistical data, age, insurance, weight, procedure types, information relating to the current and historical health, medical conditions and medical tests of its subject. In addition, EHR 122 may contain data about medical referrals, medical treatments, medications and their application, and other non-clinical administrative information, etc.

Medical information processing center 102 may further provide a medical adviser 130 as a user interface. Medical adviser 130 may be a stand-alone application, a web-based application or applet, or some other format for allowing authorized entities, including the patient, to interact, update, query and receive information from the medical information processing center 102.

Medical information processing center 102 may provide an alert generator 132 that may generate an alert to be sent to the patient, a physician, or other external entities 112 in the event of, for example, a potentially dangerous drug interaction, an emergent public health issue, or other situations requiring immediate or timely follow-up by a patient, government agency, physician, or other entity. The alert may be, for example, an e-mail, a text message, an SMS, an MMS, an instant message, a phone call, a pager alert, or a priority mailing, etc.

Medical information processing center 102 may be in communication with a patient personal medical device (PMD) 134. PMD 134 may store the patient's medical records, and may communicate with medical information processing center 102 through various methods, such as, for example: a coupling to a computer that is connected to a network, e.g. via a reader, a USB cable, a PCMCIA slot, a CD-ROM or DVD-ROM drive; a wireless connection, such as, e.g., a BLUETOOTH® or cell phone connection; or other electronic communication means. PMD 134 may provide an entry point for the entry, updating of and access to the patient's medical information in medical information processing center 102. PMD 134 is discussed further below.

Databases

Medical information processing center 102 may analyze medical information and data and may use a methodology based on fuzzy logic techniques, according to an exemplary embodiment, which may integrate fuzzy set theory with a crisp (i.e. not fuzzy) relational database, which may include the patient medical information , and may automatically generate a series of fuzzy tables. These fuzzy tables may be queried, according to an exemplary embodiment, or retrieved for more crucial decision making, or health information.

Medical information processing center 102 may have several databases, or other repositories of data and information. While the term "databases" is used herein, other methods and systems of data storage and retrieval, such as, e.g. flat databases, relational databases, flat tables, spreadsheets, text files, and/or proprietary data structures and formats, are contemplated and possible.

Exemplary databases may include a patient medical information (PMI) database 104 for holding medical information for each patient. If the patient also has a personal medical device (PMD) 134, the patient's medical data may also be stored or accessible on the medical device. The PMI database 104 may be used for storing, querying and retrieving pertinent facts, findings and observations about an individual's health history, including, e.g., past and present illnesses, examinations, tests, treatments, and outcomes. Medical information may include a patient's medical records or data, such as, e.g., patient's identification information, complaints, lab orders, medications, diagnoses, or procedures.

A patient medical record may include, but is not limited to, e.g. ECG reports; hospitalizations; diagnosis ICD; cardiac reports; emergency room (ER) visits; procedure CPT; operative reports; discharge summaries; radiology reports; consultations; medications; laboratory reports; history and physicals; allergies; and demographics.

Another database may be a medical decision fuzzy database 106 for holding up-to-date medical recommendations and decisions. According to an exemplary embodiment, the fuzzy database 106 may be used as a means of quick decisions or actions to be taken in case of emergency, as well as a source of personal health information presented in an easy to read and understand way.

The fuzzy methodology, according to an exemplary embodiment, may generate an automated and dynamic fuzzy database 106 from an existing PMI database 104.

Another database may be a medical center database 108 which may be a knowledge base that may contain "fuzzy" rules compiled from various sources which may represent what may be known about a given health problem. The main sources of these rules are medical doctors, medical research and other related areas. A method of inference may be established which may allow any query about any health problem by combining all relevant rules appropriate to answering that query. Medical center database 108 may include data from the PMI database after AI processing. As will be discussed further below, such processing may include, for example, "fuzzifying" the PMI data.

Another source of data may be one or more standard medical guidelines databases 110 containing medical information and resources, such as, for example, standard medical guidelines from various entities such as American College of Cardiology New Journal of Medicine, The Lancet, The American College of Physicians, etc.; pharmaceutical guidelines; government regulatory guidelines; health preventative guidelines; medical condition descriptions; insurance guidelines; medical journals; research reports; international classification of diseases (ICD) codes; current procedural terminology (CPT) codes; or consensus medical committee guidelines.

External Entities

Figure 2:
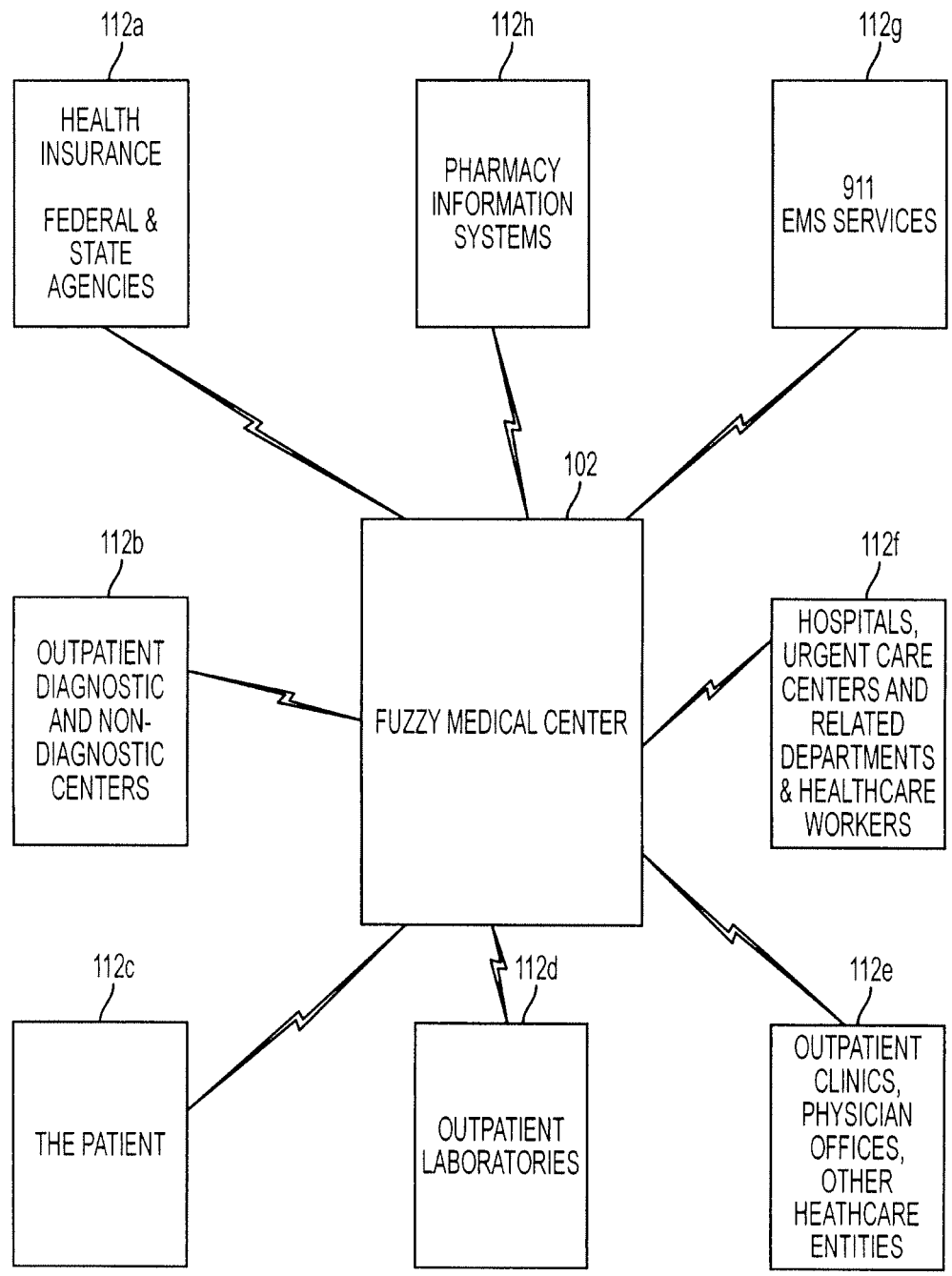
FIG. 2 depicts a block diagram of exemplary authorized external entities according to embodiments of the present invention.

Medical information processing center 102 may communicate with a number of different external entities 112, as seen in FIG. 2. Exemplary lightning bolts may represent software, hardware, networked, electronic, physical scanning, or other interfacing of information, i.e., not limited to electronic communication. Such entities may include, for example: health insurance providers, federal agencies, state agencies, regulatory agencies 112a; outpatient diagnostic clinics 112b; the patient himself 112c; medical laboratories 112d; outpatient clinics, health clinics, physicians, physicians' offices, nurses, physician's assistants, dentists, health care workers, home health aides, etc. 112e; hospitals and urgent care facilities 112f; emergency management systems 112g, e.g. 911 in the U.S.; or pharmacies or pharmacy information systems 112h. In order to comply with the Health Insurance Portability and Accountability Act of 1996 ("HIPAA") of the United States, or comparable regulations in other countries, communications with such external entities may require proper authorization and authentication prior to the transfer of confidential patient information.

Other authorized entities may include, for example, regulatory or other agencies, health care industry members (including, e.g., physicians, third party payers, government and civil agencies, etc.), which may use the system to guide, review, and monitor patient care for compliance with standards of care and patient care management.

Another authorized entity may include, for example, a patient's representative, such as an attorney or guardian, where the system may provide data during a dispute such as a malpractice case.

Artificial Intelligence (AI) Components

Exemplary embodiments of the present invention may use artificial intelligence (AI) processes to analyze medical data for diagnostic purposes as well as to identify potential health issues, suggest treatment options, follow-up testing and provide other information in support of a patient's health care providers.

Embodiments of the present invention may include an AI conduction component 118. The AI conduction component 118 may process the information coming in to the medical information processing center 102. Employing any and all available spoken and computer programming languages, diagnostic and treatment protocols, methodologies, platforms, servers, networks, internet, static and dynamic databases, and any available information in an applicable healthcare delivery system, the AI conduction component 118 may provide frequent updates, or a real-time feed of information to the medical information processing center 102.

Further, conventionally, electronic medical records and electronic health records are disjoint. The AI conduction component 118 may provide bridging of medical information of the electronic medical record 120 (EMR) and electronic health record 122 (EHR) systems. The AI conduction component 118 may maintain a variety of relationships with the external entities 112. A relationship with an entity may be continual, not always mutually exclusive, bidirectional, dynamic, non-partial, partial, complementary, or part assimilatory in the relationship's constitution and execution of the relationship's AI derivations. The AI conduction component 118 may not be a passive conduit, but instead may provide an AI filter and bridge from a healthcare delivery system to the medical information processing center 102. The AI conduction component 118 may transmit a patient's medical information and other pertinent patient information, such as demographics and ECG readings, to the medical information processing center 102 from one or more external entities 112.

A primary analytical AI component may be the AI derivation component 124, which may be a self-learning entity using AI to form derivatives and derivations of the acquired information in the medical information processing center 102. AI derivation component 124 may include medical analysis algorithms including AI processing, for example, fuzzification processing for fuzzy logic. AI derivation component 124 may rely partly on AI conduction component 118 to process information. For example, this information can be ICD codes, CPT codes, medical history, laboratory, radiology, and any pertinent medical information.

AI derivation component 124 may employ several protocols that provide information to the physician, the medical information processing center 102, and any other related health care delivery domain, for example, a diagnosis protocol 126, and a therapy protocol 128. These protocols may be correctly derived from the standard medical guidelines and algorithms, the physician recommendations, and medical experts of the field.

AI derivation component 124 may create the basis of recommendations from information from clinical human experiences and AI-derived information that is placed in a fuzzy logic context. For example, if a patient develops a life threatening iodine dye allergy reaction (anaphylactic reaction) in the hospital, embodiments of the invention will alert his primary care physician, as well as any radiology center the patient would use in the future so he would avoid exposure to iodine dye exposure.

AI derivation component 124 may be able to provide different information about the same diagnosed or resulting issue to different authorized external entities. For example, a diagnosis of a condition requiring surgery may send an alert to the surgeon regarding the patient's need for the procedure, to the hospital regarding the need for scheduling resources for the procedure, to the patient's insurer regarding pre-approval for the procedure, and to the patient himself regarding the diagnosis. Each relevant authorized external entity may therefore receive an alert, automatically, specific to that entity regarding the same underlying issue.

AI derivation component 124 may use AI techniques, including fuzzy logic, to come up with a solution for a patient's medical condition based not only on raw clinical data such as EHR and EMR, but also on current clinical practices using a patient's advanced directive, demographics, ethnic, psychological, currently accepted medical guidelines and prior physician practices, and biological data, for its decision making.

AI derivation component 124 may also use the consultation, discharge summaries, history and physical examination data, and the entire EMR 120 and EHR 122 to make recommendations to all entities 112. AI derivation component 124 may provide conclusions to the physicians and entities 112 involved in a patient's care so as to provide the patient with an optimal solution for his/her medical condition.

The AI components may use artificial intelligence, e.g., fuzzy logic, for the functionality and production of the PMC 104. For example, medical information processing center 102 may contain linguistic/descriptive data for the patient's health problems, and may include analysis and diagnosis, using medical information, medication, etc. In an exemplary embodiment, medical information processing center 102 may be compiled and put into table format using intelligence, such as, e.g., fuzzy logic techniques and algorithms. According to an exemplary embodiment, fuzzy logic algorithms and techniques may enable processing by vaguely defined or linguistic variables by incorporating expert human judgment to define those variables and their relationships to each other.

Medical information processing center 102 may include a medical adviser component 130 to provide a user interface 136, which may give access, to authorized entities, to the recommendations, steps, and decisions from the doctors of a patient that may be taken under certain circumstances. The user interface 136 may require secure access via password authentication, biometric, or the like to maintain the security of the private medical information contained in medical information processing center 102.

Figure 3:
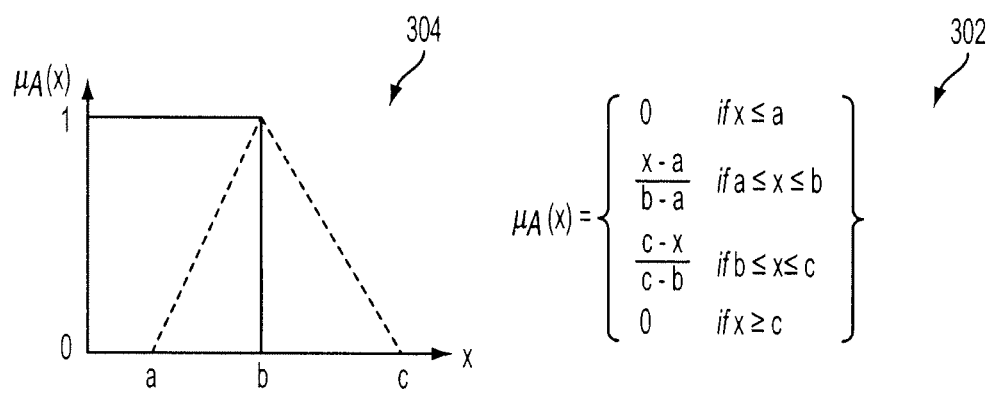
FIG. 3 depicts a fuzzy logic mathematical and programming tool fuzzy function, including a triangular membership function, as may be used according to an embodiment of the present invention.

Fuzzy logic generally includes representation of variable as a range of values, rather than as discrete values. For example, FIG. 3 illustrates an exemplary fuzzy function 302 and graph 304, which is a triangular membership function, as may be used according to an exemplary embodiment of the present invention. The function of variable x may range in value from 0 to 1, and its value may depend on a relationship between x and values a, b, and c.

Figure 4:
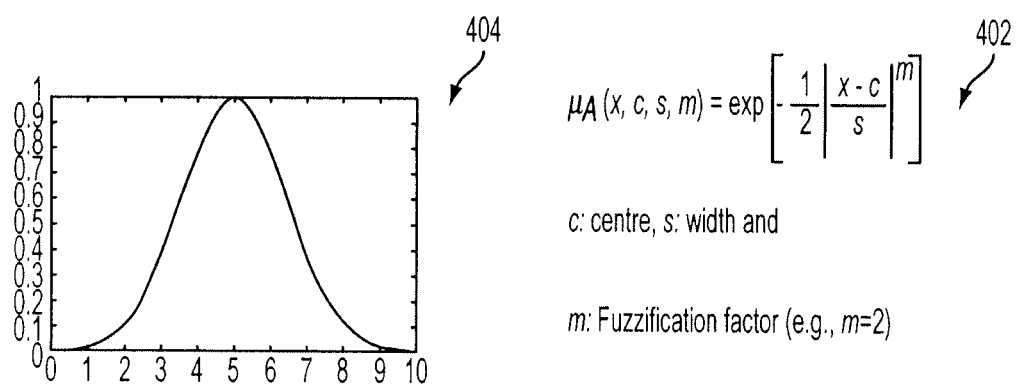
FIG. 4 depicts a fuzzy logic mathematical and programming tool fuzzy function, including a Gaussian function, as may be used according to an embodiment of the present invention.

FIG. 4 illustrates another exemplary fuzzy function 402 and graph 404, which is a Gaussian function, as may be used according to an exemplary embodiment of the present invention.

Figure 5:
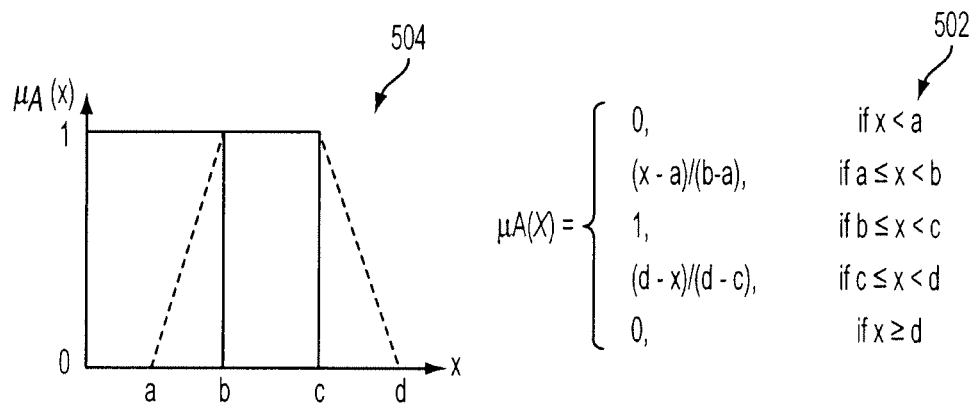
FIG. 5 depicts a fuzzy logic mathematical and programming tool fuzzy function, including a trapezoidal function, as may be used according to an embodiment of the present invention.

FIG. 5 illustrates another exemplary fuzzy function 502 and graph 504, which is an exemplary trapezoidal function, i.e. a four parameter fuzzy function, as may be used according to an exemplary embodiment of the present invention.

Figure 6:
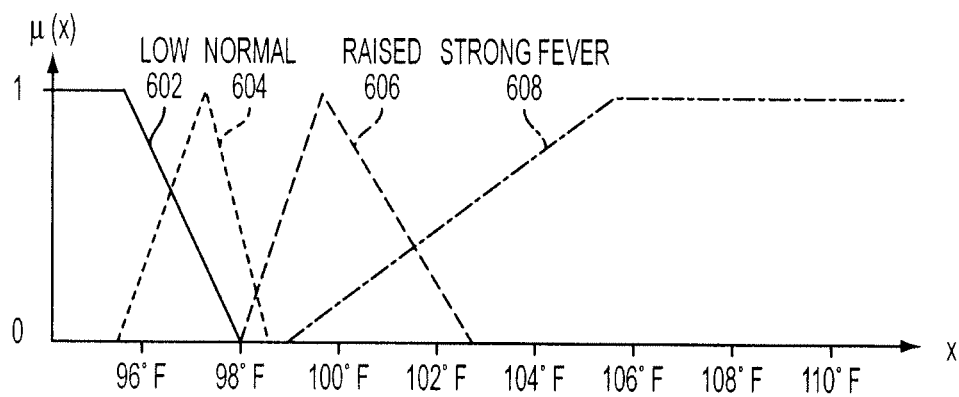
FIG. 6 depicts a fuzzy logic mathematical and programming tool fuzzy function, including a body temperature fever function including multiple fever fuzzy categories as a function of patient temperature, as may be used according to an embodiment of the present invention.

FIG. 6 illustrates a fuzzy body temperature fever function graph 602, including multiple exemplary fever fuzzy categories as a function of patient temperature, as may be used according to an exemplary embodiment of the present invention. For example, the "low" category 604 may range from 0 to 1 from patient temperature 98 degrees Fahrenheit and below. A "lower" patient temperature will have a value closer to 1. The "normal" category 606 may range from 0 to 1 for patient temperatures between 95 and 99 degrees Fahrenheit. The "raised" category 608 may range from 0 to 1 for patient temperatures between 98 and 103 degrees Fahrenheit. The "strong fever" category may range from 0 to 1 for patient temperatures above 99 degrees Fahrenheit. In an exemplary embodiment, the AI derivation component 124 may construct the body temperature fever function by analyzing patient records and standard medical guideline data 110.

In an exemplary embodiment, the AI conduction component 118 may take a patient temperature reading, for example, a reading of 99.2 degrees Fahrenheit, from PMI data 104 and "fuzzify" the reading as being more (e.g. 0.7 raised) "raised" than "normal," (e.g. 0.3 normal) especially if the patient generally has a recorded temperature of 98.6 degrees Fahrenheit. The "fuzzified" data may then be stored in fuzzy data 106.

Figure 7:
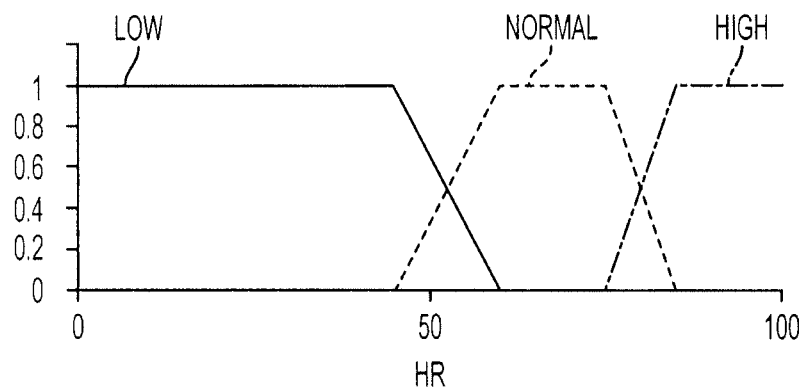
FIG. 7 depicts a fuzzy logic mathematical and programming tool fuzzy function, including a heart rate function including multiple fuzzy categories as a function of patient heart rate, as may be used according to an embodiment of the present invention.

FIG. 7 illustrates an exemplary fuzzy heart rate function including multiple exemplary fuzzy categories as a function of patient heart rate, as may be used according to an exemplary embodiment of the present invention.

Figure 8:
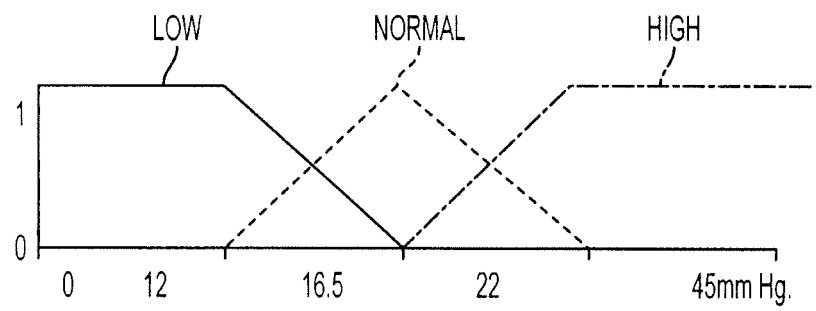
FIG. 8 depicts a fuzzy logic mathematical and programming tool fuzzy function, including an intraocular pressure (IOP) function including multiple fuzzy categories as a function of patient IOP, as may be used according to an embodiment of the present invention.

FIG. 8 illustrates an exemplary fuzzy intraocular pressure (IOP) function including multiple exemplary fuzzy categories as a function of patient IOP, as may be used according to an exemplary embodiment of the present invention.

Figure 9:
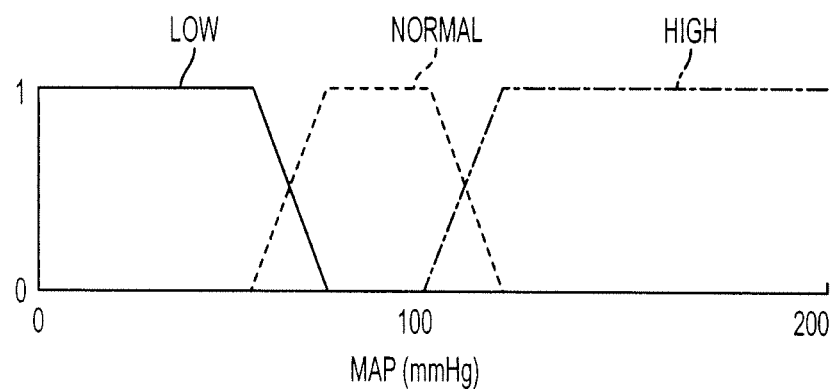
FIG. 9 depicts a fuzzy logic mathematical and programming tool fuzzy function, including a mean arterial blood pressure (MAP) function including multiple fuzzy categories as a function of patient MAP, as may be used according to an embodiment of the present invention.

FIG. 9 illustrates an exemplary fuzzy mean arterial blood pressure (MAP) function including multiple exemplary fuzzy categories as a function of patient MAP, as may be used according to an exemplary embodiment of the present invention.

The medical adviser component 130 may also allow doctors or patients to record their observations, notes, or any other health related issues for further use, according to an exemplary embodiment. The medical adviser component 130 may be also used to record new doctors/patient observations.

According to an exemplary embodiment, the AI components of medical information processing center 102 may have an intelligence learning curve. For example, the AI derivation component 124 may analyze medical information such as, e.g., the data in standard medical guideline database 110. According to an exemplary embodiment, the AI derivation component 124 may use a simple graphical user interface (GUI) and tool kits, which may allow end user modifications. According to an exemplary embodiment, the medical adviser component 130 may address all portions of the patient medical record. According to an exemplary embodiment, the documentation produced may integrate, e.g., patient demographics, clinical office(s) information, hospital(s) record information/images, treatment plans, reports, referral letters, prescriptions, or coding.

An exemplary embodiment of the present invention may also incorporate logic to continually analyze the PMI data 104 using intelligence, such as, e.g., fuzzy logic, to give, e.g., an assessment, recommendations, or an estimate of, e.g., pre-operative assessment in patients about to undergo emergency medical or surgical procedures. In an exemplary embodiment, the medical adviser 130a may also use, e.g., fuzzy logic to provide suggestions based on general and current accepted medical or health guidelines in the practice of medicine, dependent on the patient's changing medical profile. While these suggestions may not be a substitute for seeking medical advice from their physicians, the suggestions may clearly provide a means of comparison, akin to a measurement ruler, for comparison to accepted guidelines of medical care. In an exemplary embodiment, the PMD 134 may include sufficient caveats to warn users (e.g., patients, etc.) that the information may be used to supplement, or facilitate more rapid delivery or provision of, but not replace competent medical advice.

An exemplary fuzzy rule may have the following format:
IF A is B
   AND C is D
   AND E is F
   AND (G is H OR I is J)
. . .
THEN Decision.

A first example using eye exam criteria in this format is:
(I) IF "IOP" is "LOW"
　　AND CD_Ratio is "ABNORMAL"
　　AND Myopia is "HIGH"
　　THEN "Follow-up in one Month".

A second example using eye exam criteria in this format is:
(II) IF "IOP" is "NORMAL"
　　AND CD_Ratio is "ABNORMAL"
　　AND Myopia is "NORMAL"
　　THEN "Follow-up in 3 to 6 Month".

A third example using this format is:
(III) IF (SHAPE and DENSITY are positive for cancer)
　　AND Comparison with previous examinations are positive for cancer OR ( . . . AND . . . )
　　. . .
　　THEN Biopsy is recommended.

Figure 10:
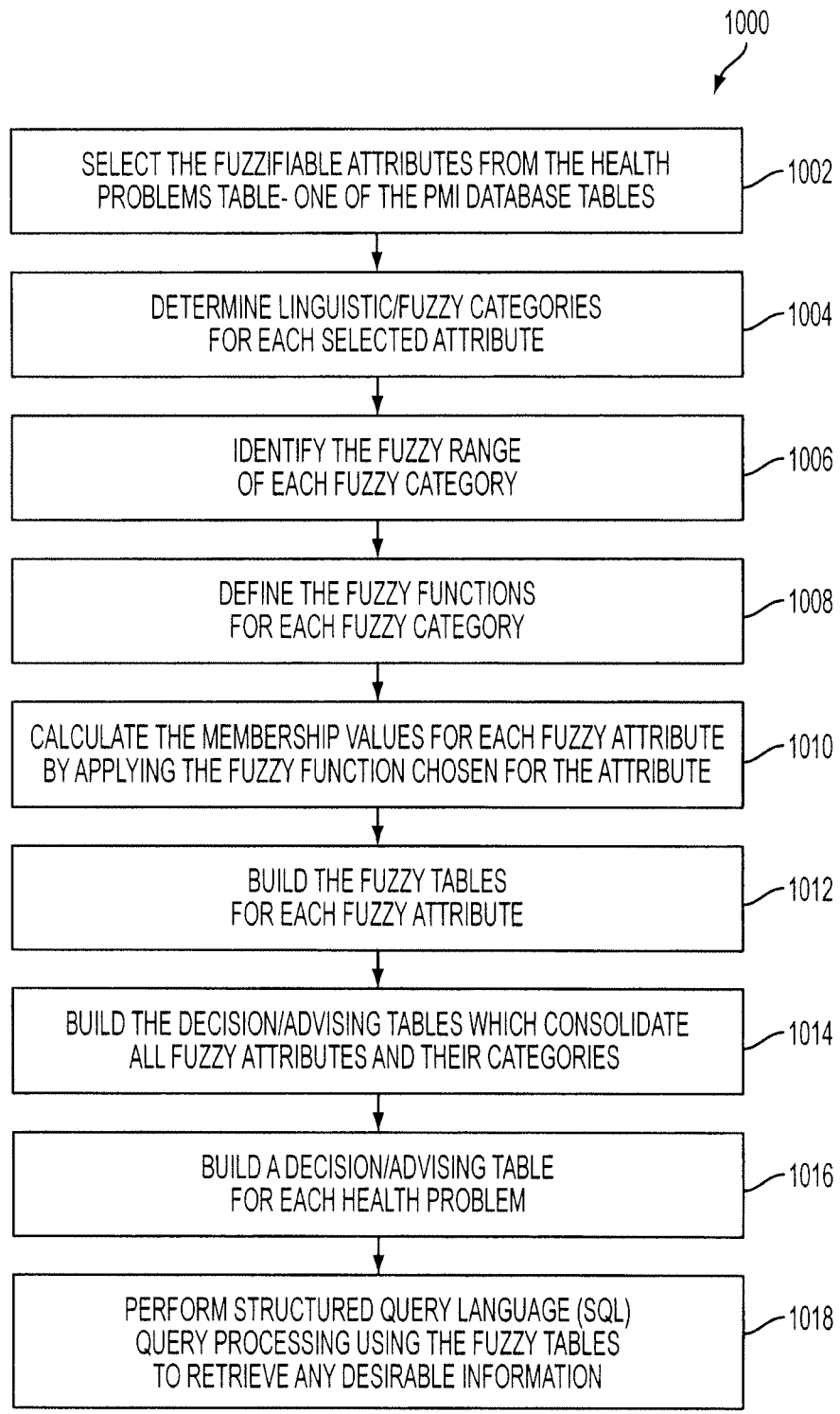
FIG. 10 depicts a flowchart of an exemplary method according to the present invention.

According to an exemplary embodiment, the dynamic medical center database 108 may be created through the following exemplary steps, as seen in FIG. 10. In block 1002, the fuzzifiable attributes from a health problems table are selected, for example, a body temperature fever attribute. The health problems table may be a part of one of the PMI database 104. In block 1004, the linguistic/fuzzy categories for each selected attribute are determined. For example, for a body temperature fever attribute, the categories may be low, normal, raised and strong fever. In block 1006, the fuzzy range of each fuzzy category is identified. For example, the range for the "low" category may be 0 to 98 degrees Fahrenheit. In block 1008, the fuzzy functions for each fuzzy category may be defined. For example, the fuzzy function $f(x)$ for the "low" category may be $f(x)=1$, if $x<95$ degrees; $f(x)=0$, if $x\geq 98$ degrees; and $f(x)=(98-x)/3$ for $95\leq x<98$. In block 1010, the membership values for each fuzzy attribute may be calculated by applying the fuzzy function chosen for the attribute. For example, a temperature reading of 99 may be a member of both the normal and raised categories, but in different degrees, based on the value of $f(x)$. In block 1012, the fuzzy tables for each fuzzy attribute are built. In block 1014, the decision/advising tables which consolidate all fuzzy attributes and their categories may be built. In block 1016, a decision/advising table for each health problem may be built. In block 1018, structured query language (SQL) query processing using the fuzzy tables may be performed to retrieve any desirable information.

In an exemplary embodiment, the PMD 134 may provide additional information, and may be used by various organizations, including, medical, health, insurance, government, civil, public or private entities, industries, institutions or domains.

User Interface

Figure 11:
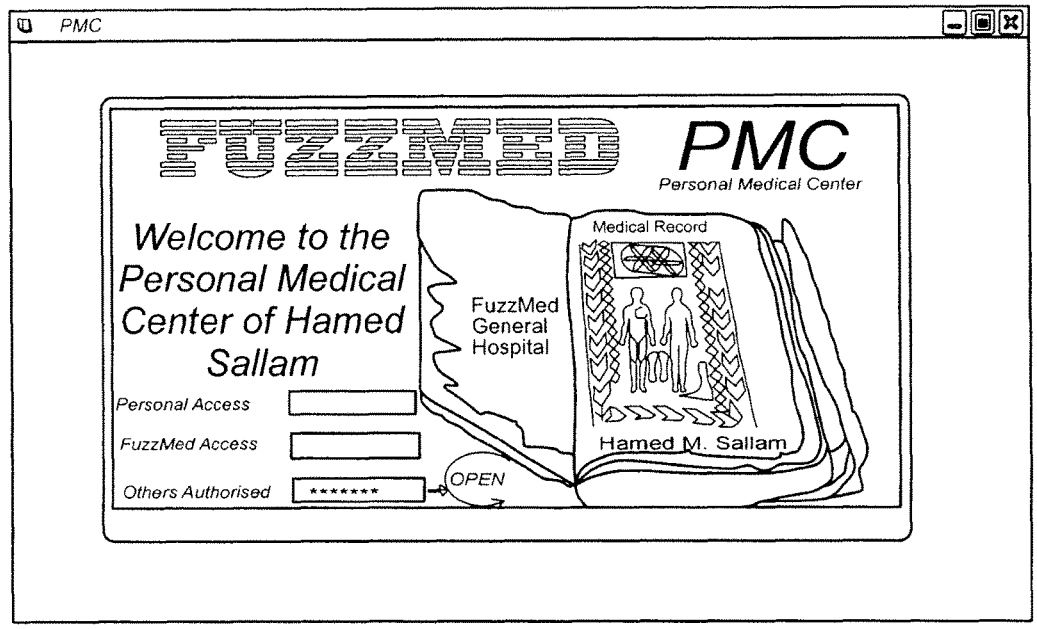
FIG. 11 depicts an exemplary screenshot of exemplary graphical user interface (GUT) of a welcome screen for access by an authorized individual to the medical center according to an embodiment of the present invention.

FIG. 11 depicts an exemplary graphical user interface (GUI) of a welcome screen for access by an authorized individual to an exemplary medical center system according to an exemplary embodiment of the present invention.

Figure 12:
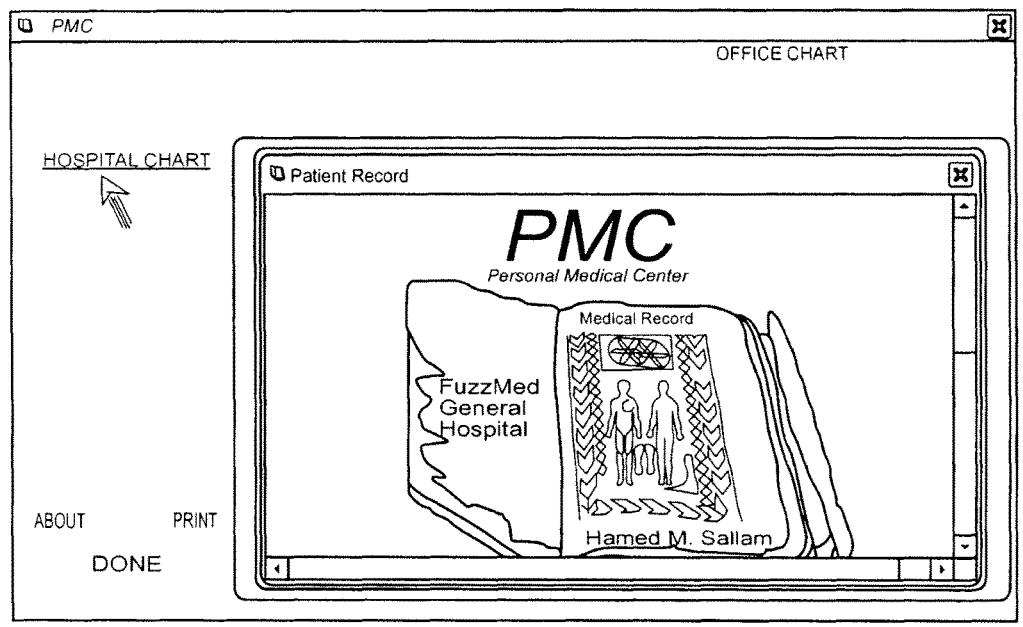
FIG. 12 depicts a screenshot of a GUI illustrating displaying a hospital chart, after the chart has been chosen of the personal medical center of an fuzzy medical center system according to an embodiment of the present invention.

FIG. 12 depicts an exemplary GUI displaying selection of a hospital chart menu selection.

Figure 13:
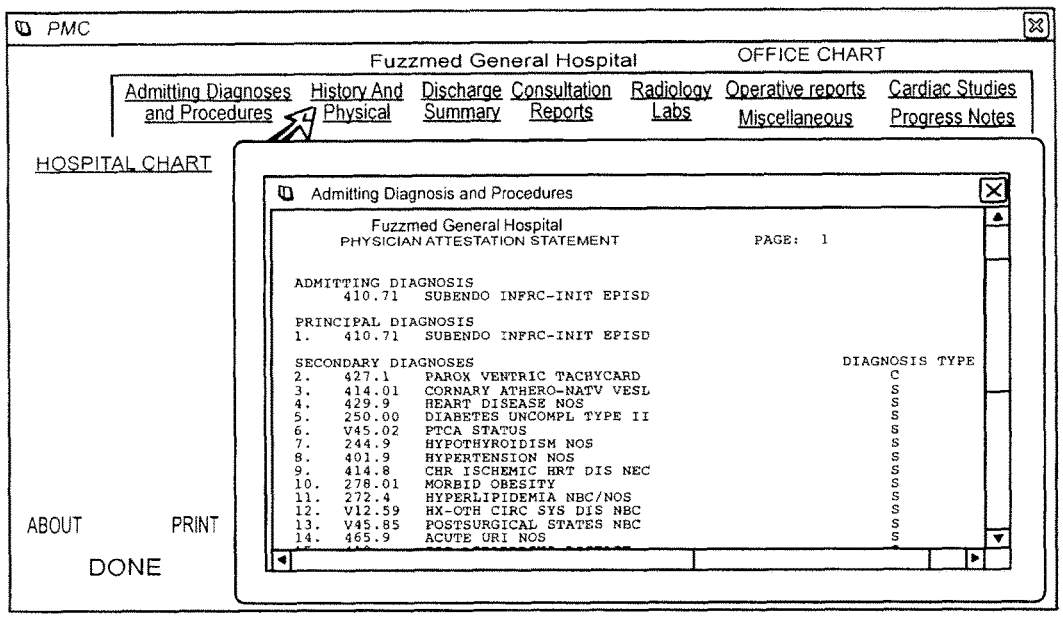
FIG. 13 depicts a screenshot of a GUI illustrating displaying a admitting diagnosis and procedure screen of the personal medical center of an fuzzy medical center system according to an embodiment of the present invention.

FIG. 13 depicts an exemplary GUI displaying an exemplary admitting diagnosis and procedure screen, available when "hospital chart" is selected.

Figure 14:
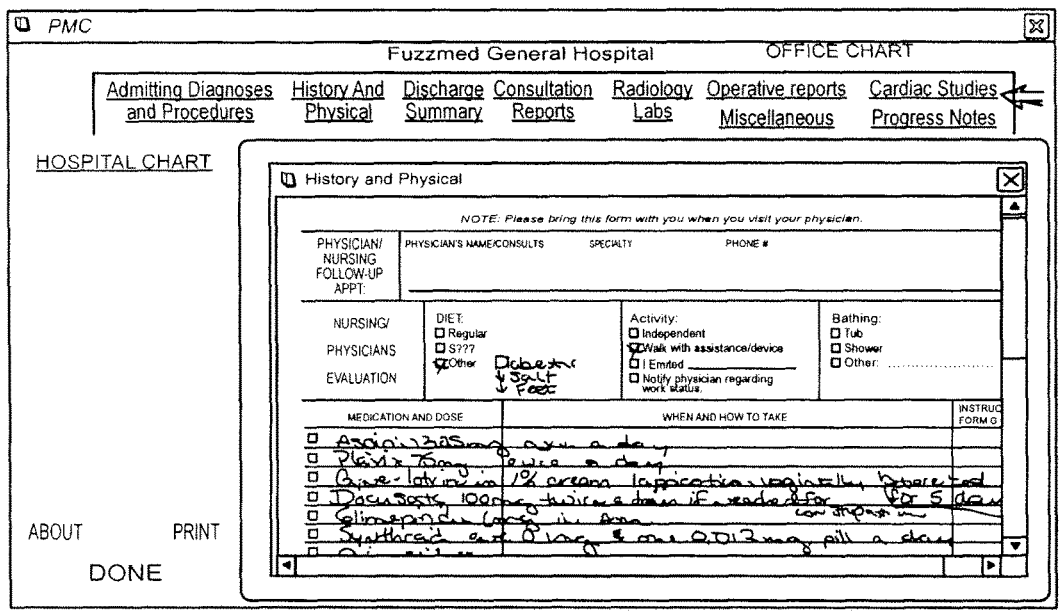
FIG. 14 depicts a screenshot of a GUI illustrating displaying a history and physical and cardiac study screen of the personal medical center of an fuzzy medical center system according to an embodiment of the present invention.

FIG. 14 depicts an exemplary GUI displaying an exemplary history and physical record.

Figure 15:
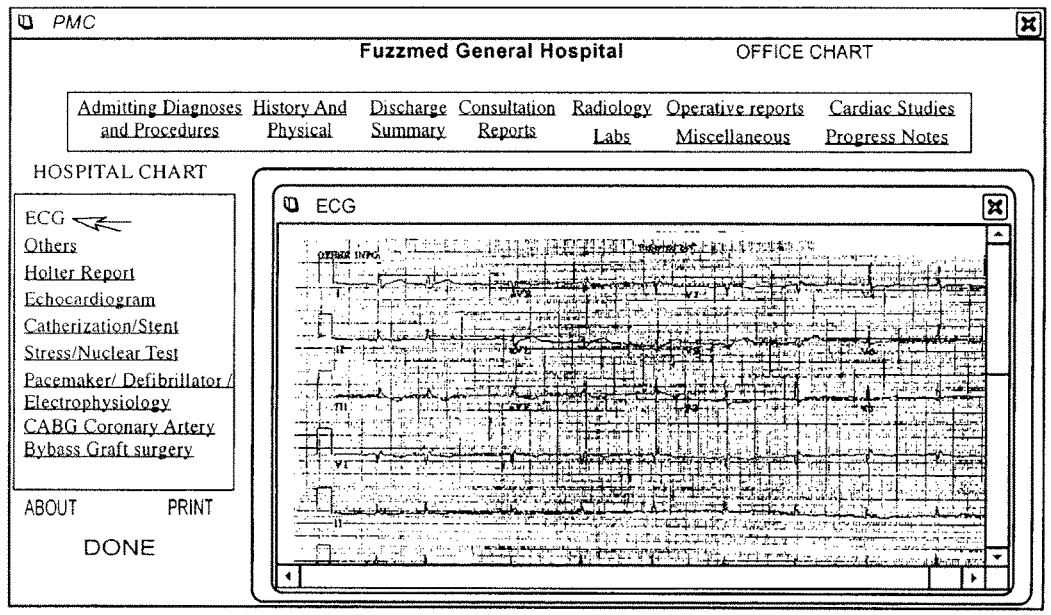
FIG. 15 depicts a screenshot of a GUT illustrating displaying a cardiac study and electrocardiogram (ECG) screen of the personal medical center of an fuzzy medical center system according to an embodiment of the present invention.

FIG. 15 depicts an exemplary GUI displaying an exemplary cardiac study and electrocardiogram (ECG) record. This record may be displayed when the "Cardiac Studies" menu selection is chosen.

Figure 16:
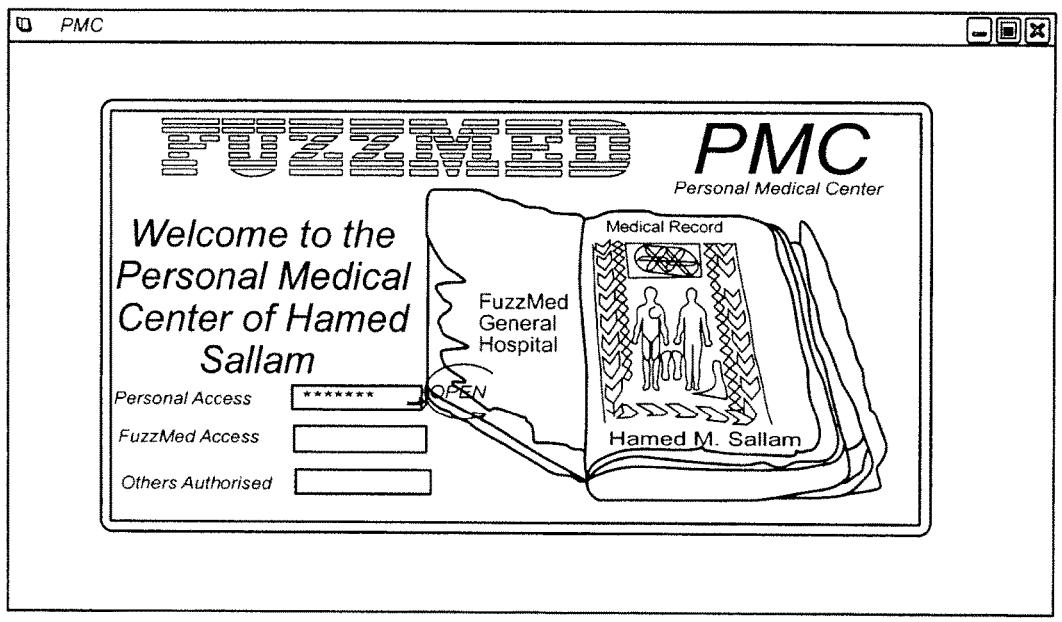
FIG. 16 depicts a screenshot of a GUT illustrating displaying a personal access session of a personal medical center (PMC) screen of an fuzzy medical center (FMC) system according to an embodiment of the present invention.

FIG. 16 depicts an exemplary GUI displaying logging into a personal access session of medical information processing center 102.

Figure 17:
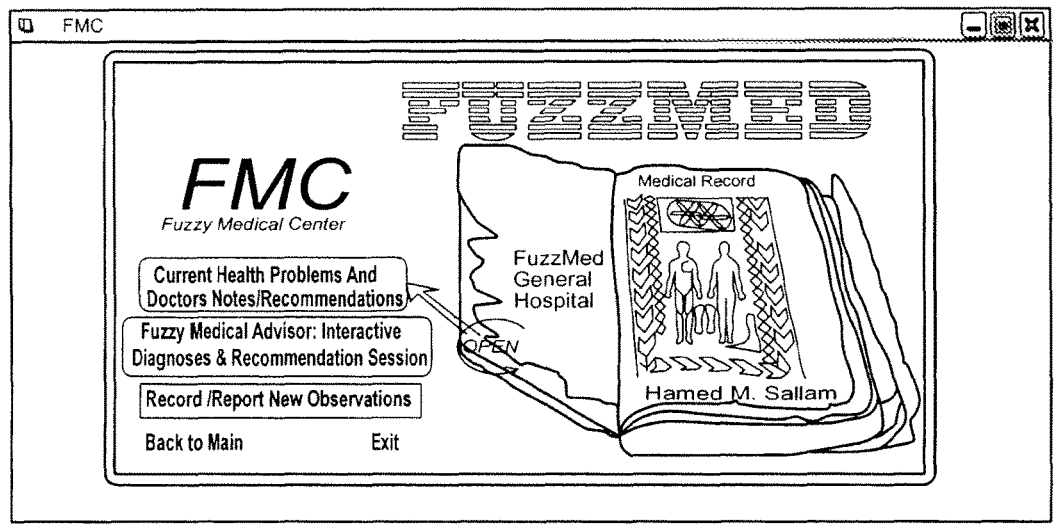
FIG. 17 depicts a screenshot of a GUI illustrating displaying a main screen of a system according to an embodiment of the present invention.

FIG. 17 depicts an exemplary GUI displaying a selection of a menu choice for an indication of current health problems.

Figure 18:
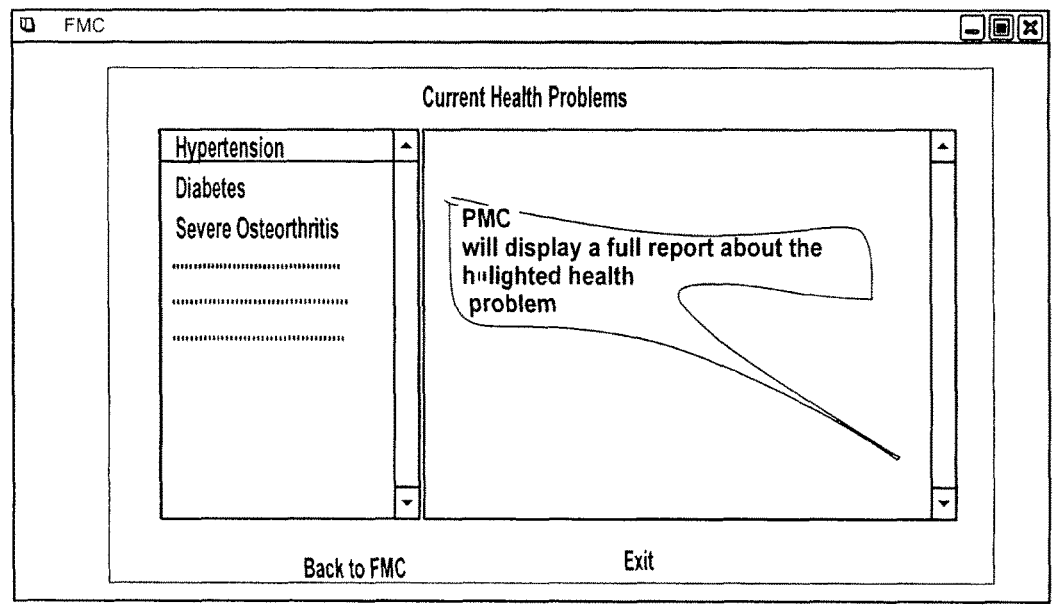
FIG. 18 depicts a screenshot of a GUI illustrating displaying a indication of current health problems, namely, in an embodiment, a hypertension screen of a medical center system according to an embodiment of the present invention.

FIG. 18 depicts an exemplary GUI displaying a list of current health problems, and a report pane for displaying a full report about a selected health problem, in this case, a hypertension report.

Figure 19:
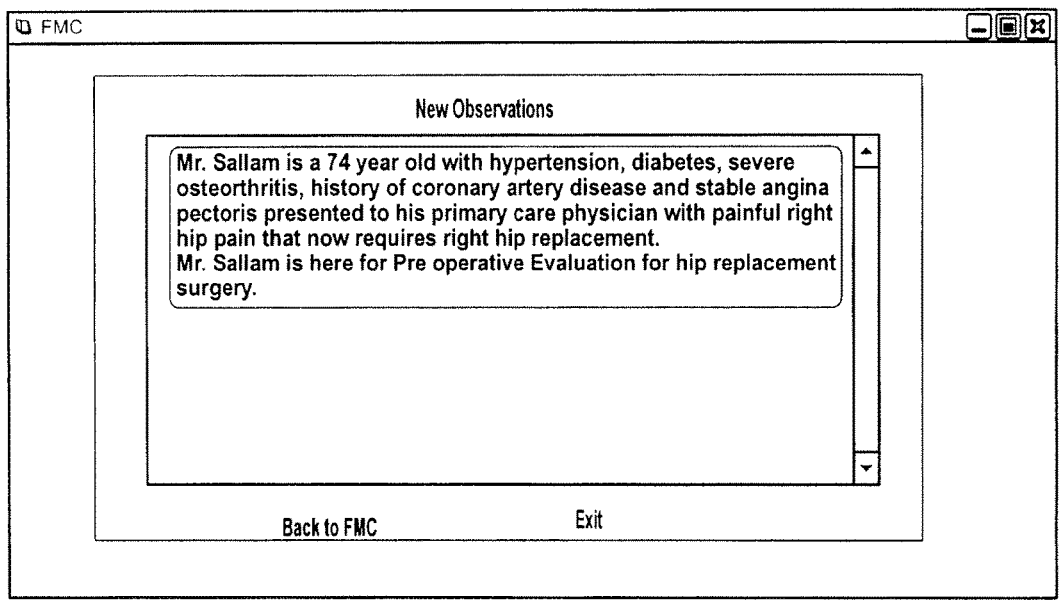
FIG. 19 depicts a screenshot of a GUT illustrating displaying a indication of current health problems, namely, in an embodiment, recording or reporting of doctor's or patient observations are shown, using a PMC screen of an fuzzy medical center system according to an embodiment of the present invention.

FIG. 19 depicts an exemplary GUI displaying a recording or reporting of doctor's or patient observations.

Figure 20:
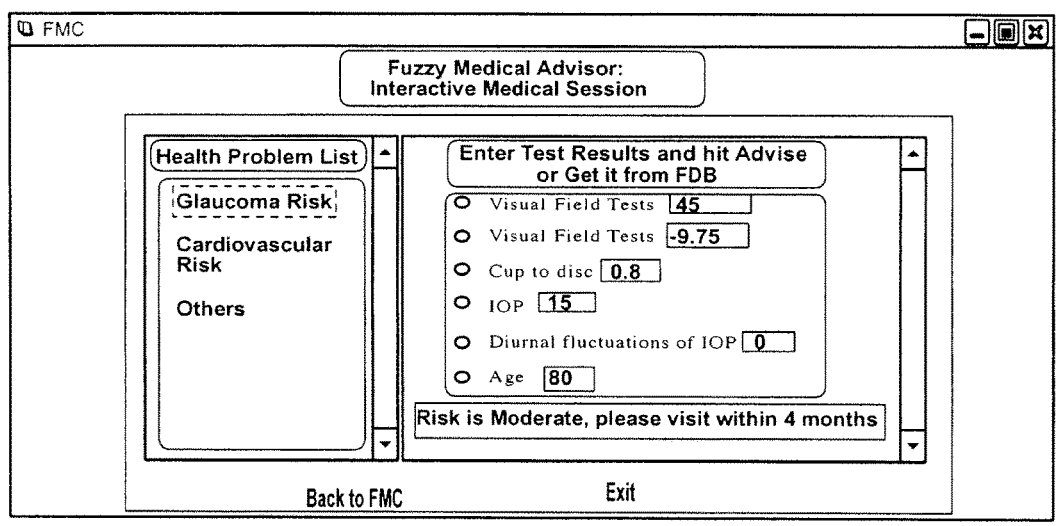
FIG. 20 depicts a screenshot of a GUI illustrating displaying a indication of analysis functionality, which in an embodiment may include fuzzy intelligence to received entry of data and to identify using fuzzy logic potential current health problems, namely, in an embodiment, a fuzzy logic medical advisor where a user may enter data, and the logic may provide fuzzy logic based feedback, as shown in the input session screen of a PMC screen of an fuzzy medical center system according to an embodiment of the present invention.

FIG. 20 depicts an exemplary GUI displaying a data entry portion of an interactive medical session through the medical adviser 130 or 103*a*. The patient may enter data manually, or retrieve data from his personal medical information or other data in medical information processing center 102. Using fuzzy intelligence and the received data, the patient's risk is assessed as "moderate" and the patient is advised to visit a physician within four months.

Figure 21:
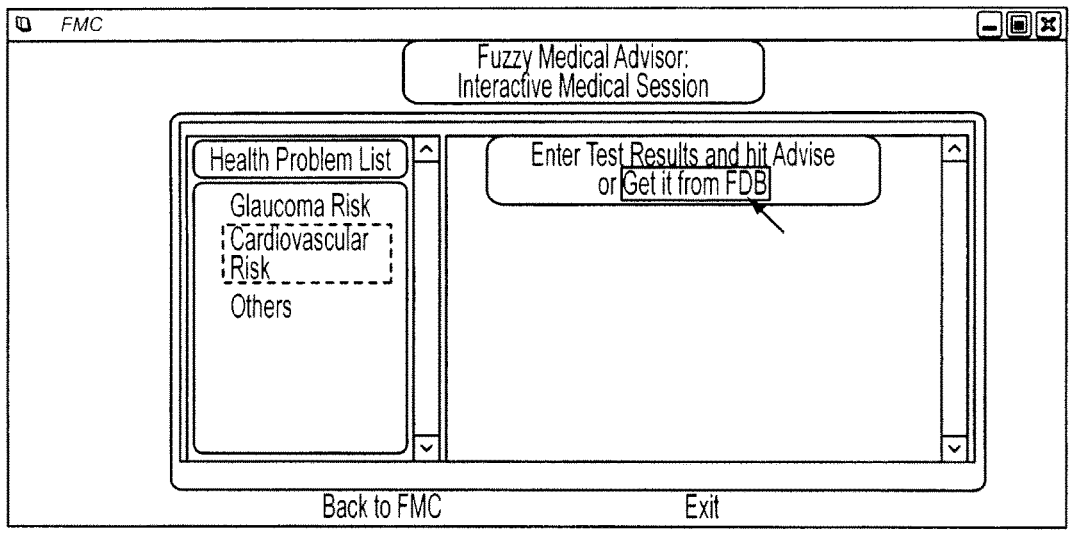
FIG. 21 depicts a screenshot of a GUI illustrating displaying an interactive medical session, in an embodiment, including, e.g., based on input data from FIG. 16, fuzzy logic may retrieve from potential output to be displayed from the fuzzy database, including as shown automatic access to the fuzzy database, using a PMC screen of a fuzzy medical center system according to an embodiment of the present invention.

FIG. 21 depicts an exemplary GUI displaying an exemplary interactive medical session, in an exemplary embodiment, including, e.g., based on input data from FIG. 21, fuzzy logic may retrieve from potential output to be displayed from the fuzzy database, including, as shown, automatic access to the fuzzy database.

Figure 22:
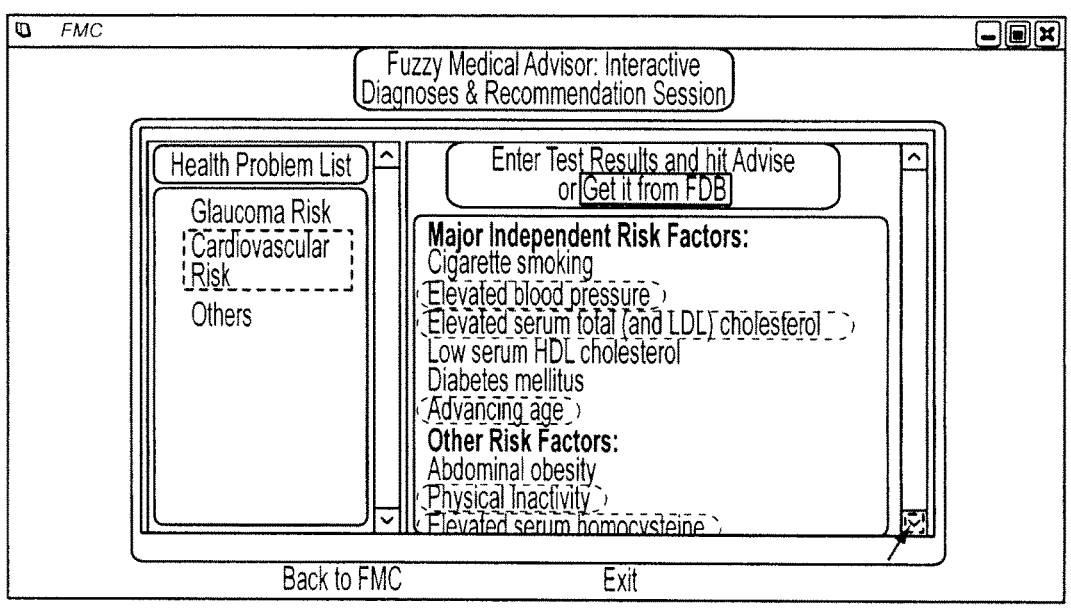
FIG. 22 depicts a screenshot of a GUI illustrating displaying a fuzzy logic analysis result including, in an embodiment, main risk factors, diagnosis and recommendations may be provided as illustratively shown, using a PMC screen of a fuzzy medical center system according to an embodiment of the present invention.

FIG. 22 depicts diagram 1800, an exemplary screenshot of exemplary GUI illustrating displaying an exemplary fuzzy logic analysis result including, in an exemplary embodiment, main risk factors, diagnosis and recommendations may be provided as illustratively shown, using an exemplary PMC 104 screen of an exemplary fuzzy medical center system according to an exemplary embodiment of the present invention.

Figure 23:
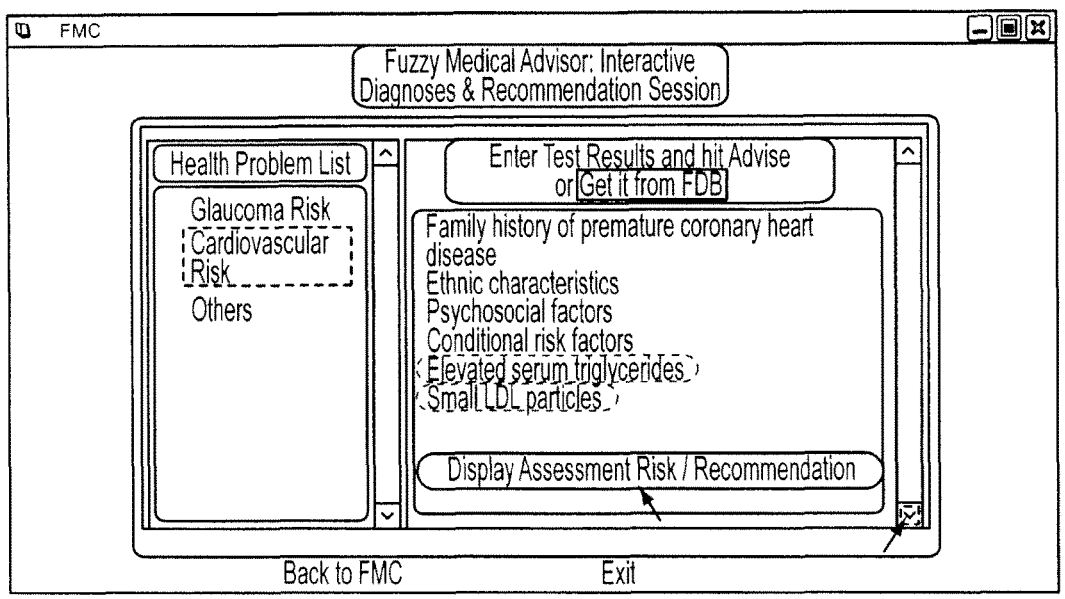
FIG. 23 depicts a screenshot of a GUI illustrating displaying a fuzzy logic analysis result including, in an embodiment, an ability to request an assessment of risk or recommendations, assessments of risk or recommendations are illustratively shown, using a PMC screen of a fuzzy medical center system according to an embodiment of the present invention.

FIG. 23 depicts an exemplary GUI displaying an exemplary fuzzy logic analysis result including, an ability to request an assessment of risk or recommendations. Assessments of risk or recommendations are illustratively shown.

Figure 24:
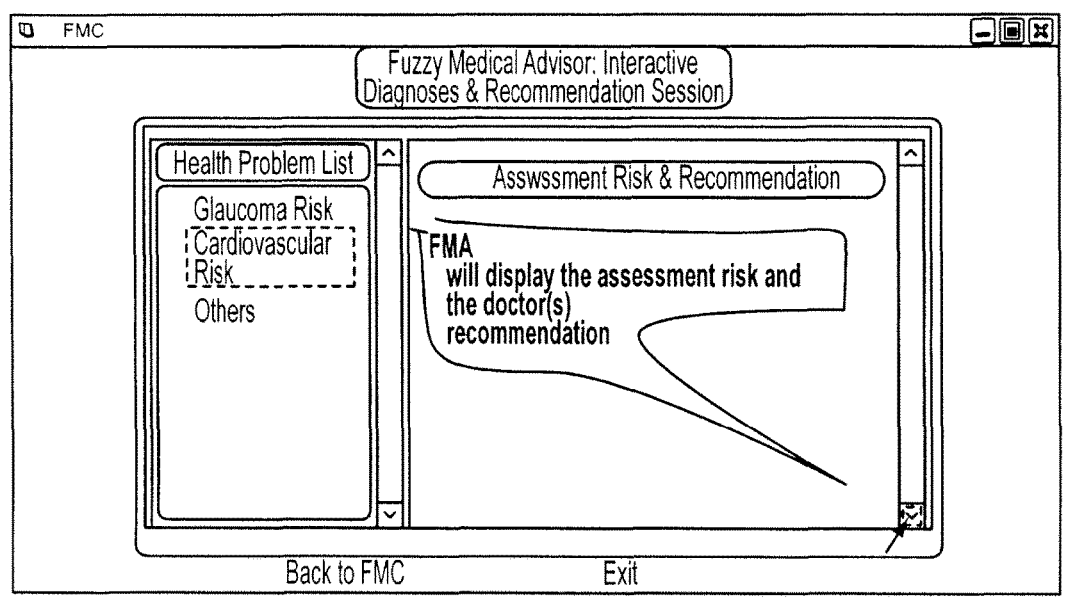
FIG. 24 depicts a screenshot of a GUI illustrating displaying a fuzzy logic analysis result including, in an embodiment, an ability to provide a fuzzy logic advisor with indications of assessment risk and doctor's recommendations based on the completed fuzzy intelligence analysis as illustratively shown, using a screen of a fuzzy medical center system according to an embodiment of the present invention.

FIG. 24 depicts an exemplary GUI displaying an exemplary fuzzy logic analysis result including an exemplary ability to provide a fuzzy logic advisor with indications of assessment risk and doctor's recommendations based on the completed fuzzy intelligence analysis as illustratively shown.

Personal Medical Device

In an exemplary embodiment, PMD 134 may be provided for storing, maintaining and processing a patient's medical information, including, e.g., capture, storage, and analysis of patient medical records, clinical information capture and management, and creation and modification of electronic medical records in the clinical environment of a patient encounter, and by which analysis of patient medical data and diagnoses based on the analysis may be provided in conjunction with physician care.

According to an exemplary embodiment of the present invention, the personal medical device (PMD) 134 may be adapted to allow instant access and control by a patient to which the PMD 134 is associated. In an exemplary embodiment, the PMD 134 may be portable and may be carried by a patient. Embodiments of PMD 134 may include, e.g., communications devices, computing devices, telephony, mobile phones, PDA, handheld, laptop, notebook, iTV, location based systems, or GPS. Access to PMD 134 and to medical information processing center 102 may be provided over various network platform types including, e.g., communications networks including, e.g., voice, data, satellite, radio, digital broadband, ultra wideband (UWB), cable television (CATV), wired communications networks, wireless communications networks, direct broadcast satellite television, multichannel multipoint distribution service (MMDS), wired networks, wireless networks, wireless fidelity (WI-FI), IEEE 802.11 WLAN networks, wireless wide area networks, IEEE 802.16 WWAN networks, (WI-MAX), broadband over power line (BOPL), mobile communications voice or data communications networks, cellular networks, analog or digital cellular networks, mobile networks, packet switched networks, voice over Internet Protocol (VoIP) networks, 2G, 3G, 4G, nG, other generation networks, using various exemplary access methods including, e.g., FDMA, CDMA, GSM, GPRS, etc. networks and protocols.

The PMD 134 may include a graphical user interface (GUI) on the device itself, or may have a GUI operable on a computer when the computer is coupled to the PMD 134, for example, through a reader, a universal serial bus (USB) cable, a network, a smart card slot, or other coupling techniques. The GUI may provide the patient with the ability to view his medical information. The GUI may further provide a medical adviser functionality. The PMD 134 may further include, in an exemplary embodiment, a medical adviser 130a, which may be a duplicate version or smaller-scale version of medical adviser 130.

The medical adviser 130a or the GUI may help a patient understand his/her diagnosis and procedures of the patient's medical information. The medical adviser 130a may compose a profile of the patient using informatics based on exemplary diagnosis and procedures for, e.g., the patient, physician, insurance provider, or any authorized entity involved in the patient's care. According to an exemplary embodiment, the records may be scanned, indexed and organized through fuzzy logic to provide a summarized concise medical profile of the patient.

The GUI may be, e.g., a notebook metaphor software application for providing user interactive access to patient medical information 104a. Although described in an exemplary embodiment using a software application, the GUI may instead be any of various well known interfaces including, e.g., a browser based interface, a web-based interface, a standalone application based interface, a software interface, a middleware interface, a client-server based application, an applet, a JAVA application or applet, a text based interface, an animated interface, a multimedia interface, a video enhanced interface, an audio enhanced interface, an application service provider application, a telephony input/output (I/O) interface (I/F), a communications I/O I/F, a computing device I/O I/F, a personal digital assistant (PDA) I/O I/F, a hardware, software, firmware, or combination of any of hardware, software and firmware based interfaces, etc.

The PMD 134 may include, in an exemplary embodiment, a storage device capable of receiving storage media which may be interactively accessed (e.g., storing medical information).

The PMD 134 may include, in an exemplary embodiment, a medical information database 104a (which may be in an exemplary embodiment, a software module). The medical information database 104a may maintain data including, in an exemplary embodiment, the personal medical information (PMI) data of the patient and other patient information. In an exemplary embodiment, the medical information database may include, but is not limited to, one or more patient medical records. PMI data 104a may mirror the patient's medical data on PMI database 104.

In an exemplary embodiment, each patient's medical chart may be evaluated and the user may have an option for the medical adviser 130a to provide, e.g., analysis, diagnoses, or suggestions of improved care or management.

In an exemplary embodiment, cardiovascular or a general health profile may be captured and maintained on the PMD 134, which may be based on each patient's unique medical history, medical information, or problems.

In an exemplary embodiment, the present invention may be cost effective to various parties, including the patient, insurance companies and medical providers, by reducing rework and improving quality of care via improved access to patient medical history, data, and information. In an exemplary embodiment, e.g., doctor's office staffs time and costs expended in reporting lab values and test results to patients may be decreased. In an exemplary embodiment, additional medical data may be interfaced to the PMD 134, to allow the patient greater access and control of the patient's own medical information. For example, medical information may be forwarded by a doctor or care provider to a patient data capture service provider, which may capture the information and provide the information to the patient on the patient's PMD 134.

In an exemplary embodiment, a patient which may be traveling abroad from the patient's place of residence, such as, e.g., outside the United States for a U.S. resident, may always have the convenience of having their entire medical records accompanying the patient, while traveling, and thus may have medical data and health history information available timely to remote caregivers, throughout the world.

In an exemplary embodiment, the present invention may reduce or eliminate redundancy and repetitive testing which conventionally may incur substantial medical costs for the health care industry. Availability of patient medical information, accompanying the patient, as the patient travels remote from the patient's residence, throughout the world, may allow for more efficient and speedy access to medical data and to medical care based on diagnosis by medical practitioners of such medical information.

In an exemplary embodiment, via logic on the PMD 134, a patient may be directed, based on analysis of particular input, to seek additional information. For example, the PMD 134, in an exemplary embodiment, may track past allergic reactions, or pharmaceutical prescriptions, and may identify potential patient allergies, or harmful drug interactions, etc. Thus, the PMD 134, by providing intelligence may encourage a patient to seek further medical attention, upon identification of particular diagnoses through device logic or intelligence. In an exemplary embodiment, the PMD 134 may include any of various well known forms of artificial intelligence (AI), including, e.g., fuzzy logic; a knowledge base (KB); a neural network; agent; software agent; a decision support system (DSS), or an expert system.

In an exemplary embodiment, the present invention may provide a constant stream of updates to the PMI database of medical information, which most databases lack, due to the requirement for labor intensive data input. By using intelligence to analyze medical data, information may be captured regarding the medical data.

In an exemplary embodiment, a fuzzy medical advisor (FMA) may be with the patient at all times and may provide the patient with analysis and advice at all times and places. In an exemplary embodiment, the medical adviser component 130 may be authentic since its analysis is based on input from the patient's medical practitioner/caregiver, and thus the data may be accurate since the data represents the patient's doctor's evaluations, recommendations and methods of treatment.

Conventionally, timeliness of access to critical medical information may usually only be available with the source of a medical data or a test (e.g., a doctor's office, hospital, or laboratory). In an exemplary embodiment, such information may advantageously be accessible to other than the source of medical data, including other users, non-source users, and including secondary users of such information.

In an exemplary embodiment, the PMD 134 may provide a communication tool between a primary physician and consultant physicians, specialists, and referred to practitioners, as their patients may carry all the patient's pertinent medical records with them to the offices.

Advantageously, the present invention may provide a fee-based service offering for which a physician's organization may obtain additional financial compensation. In an exemplary embodiment, the scanning or data capture service provider may provide this service for a fee, which may be borne by the patient, or another organization for the patient's benefit. In an exemplary embodiment, the physician may be provided a fee sharing, or revenue sharing compensation. In an exemplary embodiment, the PMD 134 may carry a subscription fee, which may be borne by a patient, creating revenues to fund provision of capture and the service, including applications, generally.

In an exemplary embodiment, fuzzy logic may be included or incorporated into the PMD 134. In addition, or in the alternative, a fuzzy logic based analysis component, such as those in medical information processing center 102, may reside on one or more servers and be in communication with the device, for example, over a network. In an exemplary embodiment, intelligence such as, e.g., the medical information processing center 102 AI components may provide diagnosis and other analysis using the patient's medical information and other sources of medical information. In an exemplary embodiment, a medical information diagnosis or procedures (such as, e.g., Current Procedural Terminology (CPT®) codes and International Classification of Diseases (ICD) codes, as will be understood to those skilled in the art, may be used to provide, analyze, and formulate a medical history that may be very pertinent and helpful for any physician, medical, caregiver, or health care provider treating the patient, as well as the patient or any other entity reviewing medical charts, which may be confusing at times.

In an exemplary embodiment, an electrocardiogram (ECG) reader for a patient may generate an ECG which may be included as part of the PMI data 104, and may be presented, in an exemplary embodiment, upon arrival at, e.g., an emergency room, for a patient with chest pain, which physicians may recognize as a vital part of a patient's medical record for a patient with known cardiovascular disease.

In an exemplary embodiment, the PMI data 104 may include, providing, e.g., a first recording of echocardiography or nuclear scintigraphy.

In an exemplary embodiment, the present invention may provide, e.g., a first personalized medical record which may analyze, extract, filter, or formulate with intelligence including, e.g., fuzzy logic technology, a digitally derived cardiovascular health profile.

In an exemplary embodiment, a cardiovascular health profile may track vital statistics of patient, which may include a patient's weight, blood pressure, cholesterol profile, or blood sugar/glycocylated hemoglobin levels, etc., and may display the doctor's recommendations.

In an exemplary embodiment, an etiology may be multifactorial. In an exemplary embodiment, the etiology may include, e.g., but may be predominantly from, e.g., genetics, hypercholesteremia, hypertension, diabetes, smoking or obesity.

In an exemplary embodiment, the present invention may include covering, e.g., all organ system checkups, which may be needed for health maintenance, such as, e.g., thyroid tests, prostate specific antigen, mammography, colonoscopy examination, pelvic exams, chest x-rays, Dexa bone scan, cell blood counts, chemistries, vaccinations, which may be needed as screens, or workup, for common medical illnesses. In an exemplary embodiment, this health profile may track, e.g., results of these tests, and may assist guiding a physician, patient, or any other entity attempting to assess the patient's overall health, including, e.g., a parent of a child, a prospective insurance provider, prospective employer, etc. (assuming a patient agrees to disclose such information to such a third party).

In an exemplary embodiment, the present invention may provide a personalized risk assessment, which may be a surgical risk assessment, or may be a pre-operative surgical risk assessment.

In an exemplary embodiment, the present invention may provide immediate information to a healthcare provider when a patient is in a dire emergency.

In an exemplary embodiment, if a patient brings the PMD 134 to a point of care, such as, e.g., a hospital, or an emergency room, the information may be used, e.g., while awaiting prior test results, may be used by a surgeon about to operate on a patient, by an insurance carrier, or by another physician requesting such medical information. The interface of the PMD 134 may be able to furnish medical information, which may be needed by the health caregiver, since the PMD 134 may be carried by the patient.

In an exemplary embodiment, the present invention may reduce the need for repeat patient testing since previously obtained medical data may be carried by the patient.

In an exemplary embodiment, the present invention may provide efficiency and may save costs with regard to patients having congestive heart failure (CHF) or coronary artery disease, as will be apparent to those skilled in the art, some of the largest financial burdens on the U.S. Medicare system.

The present invention may be particularly useful for patients with cardiovascular disease, where rapid diagnosis by health care workers is critical in the event of heart failure or other cardiovascular health related disease. In an exemplary embodiment, the system according to the present invention may allow physicians nationwide to know the past medical status of the patient and not only avoid unnecessary testing, but guide care by avoiding therapeutic modalities that might otherwise be harmful to the patient. Often, the majority of care provided to patients with coronary artery disease and CHF in hospitals is performed due to the absence (i.e., unavailability, or inaccessibility) of prior medical record data such as, e.g., echocardiograms, cauterization, stress testing, or prior cholesterol testing.

The present invention may be particularly useful for patients with chronic or complex medical histories, such as, e.g., elderly or cancer patients. Since the greater the complexity of a patient's medical history, the more likely, past medical history may be indicative of important contributions to diagnosis of a present medical condition. In an exemplary embodiment, the PMD 134 may target high risk groups and complex medical history groups.

An exemplary embodiment of the present invention is FUZZMED PATIENT MEDICAL RECORD (PMR) available from FUZZMED, INC. of Vienna, Va., USA.

In an exemplary embodiment, an electronic medical record system may be based on scanned, true copies of an original medical record of a patient and may be designed in a format that may be easily carried by the patient as the patient's own personal record as well as being available to health care workers, if offered by the patient to the worker. The PMD 134, according to an exemplary embodiment, may incorporate scanning of actual images of text, graphics, images, or pictures of the medical record, as well as index, metadata, or key frame information, and may, according to an exemplary embodiment, use fuzzy logic or other intelligent technology for providing analysis such as, e.g., formulating diagnosis or procedures which may be found in the medical record. The system according to an exemplary embodiment of the present invention, may be stored on any storage media, via a storage device, which may include, e.g., a portable device, a computing device, a personal computer (PC), a handheld device, a communications device, a telephony device, a wired or wireless device, a personal digital assistant (PDA), a card, a smart card, compact disk (CD), tape, zip, hard disk, direct access storage device, sequential access storage device, memory, flash, non-volatile storage, digital versatile disk (DVD), CD-R, DVD-R, or other device that may receive a storage medium. According to an exemplary embodiment of the present invention, a service provider may scan or capture pertinent medical record information and may store it on a storage device capable of being retrieved by a computing device, a communications device, a PC, handheld device, smart card reader, or even a network such as, e.g., but not limited to the Internet.

Entering Data into the System

According to an exemplary embodiment, medical records may be scanned and placed onto the PMD 134 or into an appropriate database in medical information processing center 102. Data and information may be automatically placed onto the PMD 134, by, e.g., downloading, etc.

According to an exemplary embodiment, medical information processing center 102 or PMD 134 may include a scanning process, and a medical record filter and digital coding for all of the scanned patient medical records. A unique, possibly proprietary, application may be provided to work on, e.g., PMD 134, a computing device, a communications device, a personal digital assistant (PDA), a Pocket PC (PPC), a smart card, a smart phone device (SPD), a telephony device, a wired or wireless device, and computers. According to an exemplary embodiment, a quality control process may apply an intelligent scanning algorithm to the scanned patient medical records to manage and enhance scanned patient's medical records, may save documents and, may include, e.g., a stamp, an electronic name or code. Metadata may be captured while capturing medical record information, and the scanned documents may be indexed.

In an exemplary embodiment features relating to scanning, capture or digitization of medical data, may be included. In an exemplary embodiment, a document digitization or imaging solution may capture or digitize documents, as well as may analyze or filter the captured or digitized documents.

According to an exemplary embodiment, the received medical records from a patient may have a computer typed page that may have essential summary information about the patient including, e.g., a first name, last name, a SSN, or other identifier, an address, emergency contact number(s), primary care physician (e.g., name/contact number), a blood type, and any high profile health risk. The medical record's pages may then be prepared for scanning, (i.e., the papers may be reviewed to ensure there are no twisted papers, to identify any cut papers and to check the size of the papers). According to an exemplary embodiment, once the medical records may have passed a first preparation line, then, a separation sheet may be included between each part of the medical record, and that sheet may have the name of the group of papers to be scanned immediately after that page. Once the separation process is done, then a barcode label may be automatically printed, i.e., indexing the document, and may be placed on the top of the first page. Alternatively, another identifier such as, e.g., a radio frequency identifier (RFID), or other identification means may be used as will be apparent to those skilled in the art.). Each barcode label may reflect, according to an exemplary embodiment, a patient's full name (last name, first name) and a social security number. According to an exemplary embodiment, the computer typed index document that may have all of the essential information, may be the first page of the medical record. Once the record has passed labeling, then it may be ready for scanning. As seen, for example, in FIG. 28, during scanning, the scanning operators may feed the patient's medical records into the scanner and the data may be captured in an image format, or the information appearing on the pages may be recognized using recognition technologies such as, e.g., optical character recognition (OCR), or other technology. Other means of capture may be used other than scanning including, photographing, using e.g., a digital camera, etc.

Part of the solution, according to an exemplary embodiment, may entail entering the essential patients' information as an index of the image, and may include storing the image and indexing data on a central database in order to generate the cover sheets that may have the essential information and identification information such as, e.g., a barcode label. By using the process according to an exemplary embodiment, a record may have been created for the patient before the scanning process, so, once the scanning process begins, then the scanned documents associated with the patient can be attached or associated with the patient name, and may be added to the patient's record.

According to an exemplary embodiment, the medical record data may be scanned and may be stored in any of various appropriate formats as will be apparent to those skilled in the relevant art. According to an exemplary embodiment, scanned images may be compressed. According to an exemplary embodiment, the captured or scanned medical data may be stored in, e.g., an Adobe Acrobat portable document format (PDF), Motion Picture Experts Group (MPEG) (for video information) or a Joint Photographic Experts Group (JPEG) formats. The scanned medical records may be stored on/accessed via a storage medium on a storage device such as, e.g., a computer hard drive (HD), Secure Digital card (SD) or a Smart Card (SCC). The user interface 136 may be used to access (e.g., to retrieve) any medical information from one of the storage media (e.g., SD, SCC & HD, etc.). According to an exemplary embodiment, scanned images may also be encrypted. Access to the scanned image data may be restricted using security technology to protect privacy of the data. Exemplary technologies to control access may include the use of encryption, hash codes, public key encryption, use of passwords, biometrics (e.g., such as, e.g., fingerprint readers, iris readers, voice recognition systems, etc.). Authorized external entities may be required to authenticate themselves to the system prior to accessing a patient's records.

According to an exemplary embodiment, medical information processing center 102 may include a search facility to search metadata, indices, or other searchable aspects of the contents of each captured page or medical data. Because not all medical record pages are the same, and each page's format may be different, medical information processing center 102, according to an exemplary embodiment, may have its own searching capability to search within each page of the patient medical record. Patients' medical records are very important documents, may contain private information, may include sensitive information, may hold a medical history of a patient, and thus access to this information must be controlled carefully. Since the contents of the documents may have legal implications (e.g., malpractice, etc.) it may be provided, in an exemplary embodiment, that the files may be set to a read only status, to avoid making any changes to the documents. The medical record data may reflect that a patient has visited a doctor's office, a hospital or immediate medical care facilities; all this and other information may also get added into the patient's medical history. It may be very important to keep the scanned documents free of any modifications or changes to the contents thereof. However, it may be useful to include indexes, metadata and bookmarks in the scanned documents to allow ease of access to the underlying data and information shown on the medical information documents in the scanned files. Thus, search capabilities may be enabled within a medical record, even if the appearance of the scanned document is prevented from being modified by the use of embedded metadata, etc, as will be apparent to those skilled in the relevant art.

According to an exemplary embodiment, medical information processing center 102 may include integrated fuzzy logic algorithms that may electronically label each scanned page, and contents within a subset of the page of the medical records. According to an exemplary embodiment, the present invention may capture various information about a document being captured. In addition to previously mentioned information from above, according to an exemplary embodiment, medical information processing center 102 may facilitate providing information to users, for use by, e.g., medical doctors, medical emergency services/facilities, healthcare provider or patients. Such information may include, for example: name and demographics (face sheet); allergies and blood type; medications; most comprehensive list of prior diagnosis given to this patient (ICD codes); most comprehensive of CPT codes given to this patient pertaining to medical and surgical procedures excluding office visits; date; electrocardiogram (ECG); vital signs; or blood work, CBC, Chem32 (chem7 and LFTS), PT/PTT/INR, or chest X ray.

The order of providing the above information may also be relevant, as the ordering may be the order preferred by emergency room (ER) and ambulance paramedics. By providing this information in a rapid, immediately available and expected form, embodiments of the present invention may be able to provide this most important information rapidly, and may yet in a comprehensive way enable understanding a patient, in less than about three minutes. The CPT codes and ICD codes may be obtained using, e.g., intelligence, such as, e.g., fuzzy logic algorithms, for use with each patient, according to an exemplary embodiment.

Exemplary Embodiment of Computer Environment

Figure 25:
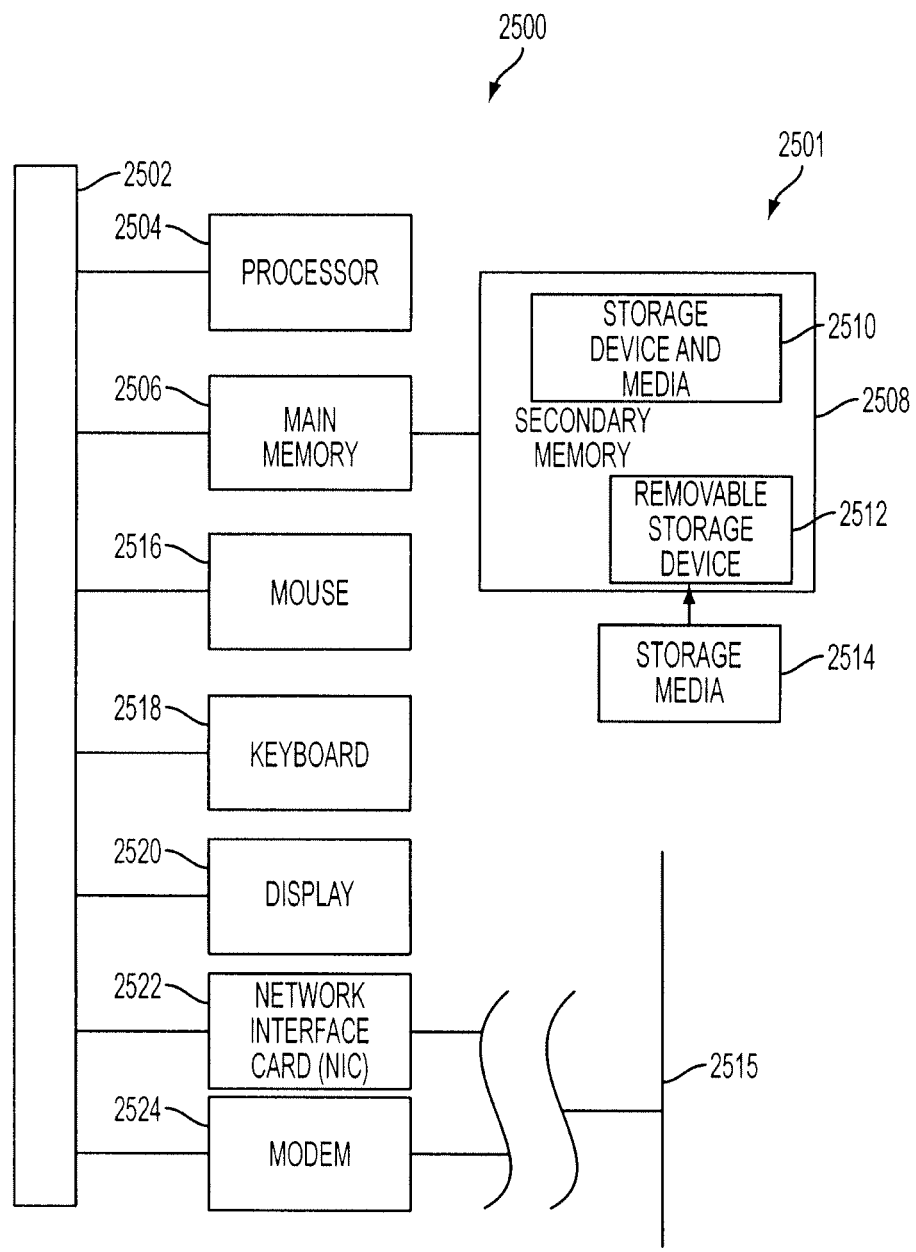
FIG. 25 depicts an exemplary computing device as may be used as a PMI device, according to an exemplary embodiment of the present invention.

FIG. 25 depicts an exemplary computer system that may be used in implementing an exemplary embodiment of the present invention. Specifically, FIG. 25 depicts an exemplary embodiment of a computer system 2500 that may be used in computing devices such as, e.g., client or server, etc. according to an exemplary embodiment of the present invention. FIG. 25 depicts an exemplary embodiment of a computer system that may be used as client device 102 or a server device 104, etc. The present invention (or any part(s) or function(s) thereof) may be implemented using hardware, software, firmware, or a combination thereof and may be implemented in one or more computer systems or other processing systems. In fact, in one exemplary embodiment, the invention may be directed toward one or more computer systems capable of carrying out the functionality described herein. An example of a computer system 2500 is shown in FIG. 25, depicting an exemplary embodiment of a block diagram of an exemplary computer system useful for implementing the present invention. Specifically, FIG. 25 illustrates an example computer 2500, which in an exemplary embodiment may be, e.g., (but not limited to) a personal computer (PC) system running an operating system such as, e.g., (but not limited to) MICROSOFT® WINDOWS® NT/98/2000/XP/CE/ME/etc. available from MICROSOFT® Corporation of Redmond, Wash., U.S.A. However, the invention may not be limited to these platforms. Instead, the invention may be implemented on any appropriate computer system running any appropriate operating system. In one exemplary embodiment, the present invention may be implemented on a computer system operating as discussed herein. An exemplary computer system, computer 2500 is shown in FIG. 25. Other components of the invention, such as, e.g., (but not limited to) a computing device, a communications device, mobile phone, a telephony device, a telephone, a personal digital assistant (PDA), a personal computer (PC), a handheld PC, an interactive television (iTV), a digital video recorder (DVD), client workstations, thin clients, thick clients, proxy servers, network communication servers, remote access devices, client computers, server computers, routers, web servers, data, media, audio, video, telephony or streaming technology servers, etc., may also be implemented using a computer such as that shown in FIG. 25. Services may be provided on demand using, e.g., an interactive television (iTV), a video on demand system (VOD), and via a digital video recorder (DVR), or other on demand viewing system.

The computer system 2500 may include one or more processors, such as, e.g., processor(s) 2504. The processor(s) 2504 may be connected to a communication infrastructure 2506 (e.g., a communications bus, cross-over bar, or network, etc.). Various exemplary software embodiments may be described in terms of this exemplary computer system. After reading this description, it will become apparent to a person skilled in the relevant art(s) how to implement the invention using other computer systems or architectures.

Computer system 2500 may include a display interface 2502 that may forward, e.g., graphics, text, and other data, etc., from the communication infrastructure 2506 (or from a frame buffer, etc., not shown) for display on the display unit 2530.

The computer system 2500 may also include, e.g., but may not be limited to, a main memory 2508, random access memory (RAM), and a secondary memory 2510, etc. The secondary memory 2510 may include, for example, (but not limited to) a hard disk drive 2512 or a removable storage drive 2514, representing a floppy diskette drive, a magnetic tape drive, an optical disk drive, a compact disk drive CD-ROM, etc. The removable storage drive 2514 may, e.g., read from or write to a removable storage unit 2518 in a well known manner. Removable storage unit 2518, also called a program storage device or a computer program product, may represent, e.g., a floppy disk, magnetic tape, optical disk, compact disk, etc. which may be read from and written to by removable storage drive 2514. As will be appreciated, the removable storage unit 2518 may include a computer usable storage medium having stored therein computer software or data.

In alternative exemplary embodiments, secondary memory 2510 may include other similar devices for allowing computer programs or other instructions to be loaded into computer system 2500. Such devices may include, for example, a removable storage unit 2522 and an interface 2520. Examples of such may include a program cartridge and cartridge interface (such as, e.g., those found in video game devices), a removable memory chip (such as, e.g., an erasable programmable read only memory (EPROM), or programmable read only memory (PROM) and associated socket, and other removable storage units 2522 and interfaces 2520, which may allow software and data to be transferred from the removable storage unit 2522 to computer system 2500.

Computer 2500 may also include an input device such as, e.g., (but not limited to) a mouse or other pointing device such as a digitizer, and a keyboard or other data entry device (none of which are labeled).

Computer 2500 may also include output devices, such as, e.g., (but not limited to) display 2530, and display interface 2502. Computer 2500 may include input/output (I/O) devices such as, e.g., (but not limited to) communications interface 2524, cable 2525 and communications path 2525, etc. These devices may include, e.g., a network interface card, and modems (neither are labeled). Communications interface 2524 may allow software and data to be transferred between computer system 2500 and external devices.

In this document, the terms "computer program medium" and "computer readable medium" may be used to generally refer to media such as, e.g., removable storage drive 2514, or a hard disk installed in hard disk drive 2512, etc. These computer program products may provide software to computer system 2500. The invention may be directed to such computer program products.

Exemplary System

Figure 26:
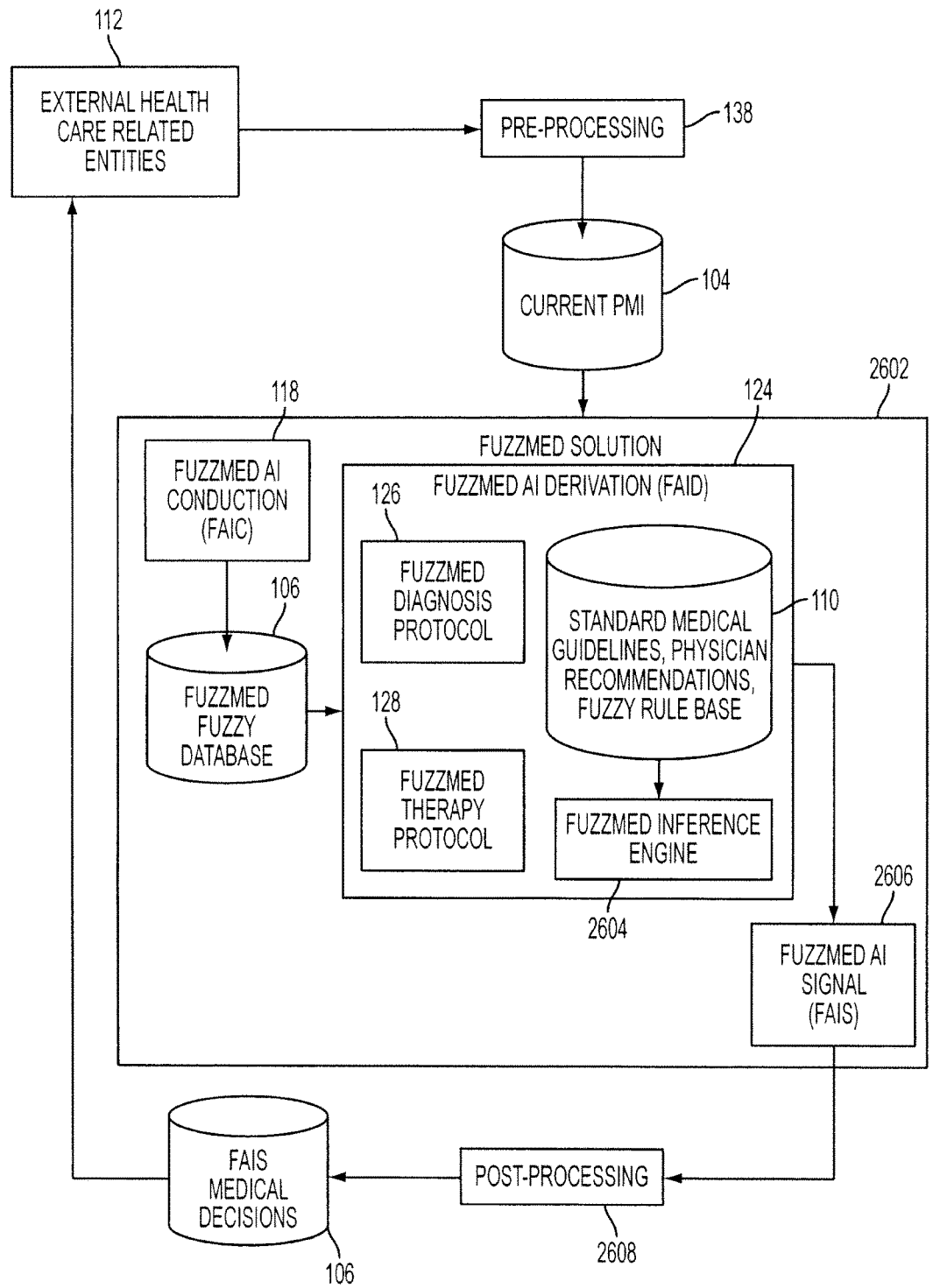
FIG. 26 depicts an exemplary specific embodiment of a system according to the present invention.

An exemplary system, referred to herein as "FUZZMED™ Solution" 2602 and process flow, as provided by FUZZMED, INC. of Vienna, Va., USA is illustrated in FIG. 26.

Data from external health care entities 112 is sent to FUZZMED™ Solution 2602 to pre-processing unit 136. Pre-processing unit 136 may be software or hardware that organizes, maintains, edits, and processes the incoming patient data and medical information. The pre-processed data may be stored in the patient medical information database 104. FUZZMED™ Artificial Intelligence Conduction "FAIC" 118 may then receive data from the PMI Database 104, convert the data, e.g. by "fuzzifying" the data, and build FUZZMED™ Fuzzy Database 106. The conversion may include formatting the data for use by FUZZMED™ Artificial Intelligence Derivation "FAID" 124. FAID 124 is the primary AI processing unit of FUZZMED™ Solution 2602, and may create and use FUZZMED™ diagnosis protocol 126 and FUZZMED™ therapy protocol 128. These protocols may be correctly derived from the standard medical guideline data 110, including the physician recommendations, and other fuzzy rules from medical experts of the field.

FAID 124 may include a FUZZMED™ inference engine 2604, which may be a hardware/software component of FAID. FUZZMED™ inference engine 2604 may be a computer program that tries to derive answers from a knowledge base. FUZZMED™ inference engine 2604 may communicate continuously with standard medical guideline data 110 to prepare the data base management system and queries for FUZZMED™ artificial intelligence signal "FAIS" 2606. FAIS 2606 is the communication channel that transmits the conclusions based on FAID 124 outcomes.

As is known the art, an inference engine, generally, may be described as a form of finite state machine with a cycle consisting of three action states: match rules, select rules, and execute rules. In the first state, match rules, the inference engine may find all of the rules that are satisfied by the current contents of the data store. When rules are in the typical condition-action form, this means testing the conditions against the working memory. The rule matchings that are found are all candidates for execution: they are collectively referred to as the conflict set. The pair of a rule and a subset of matching data items is called an instantiation of the rule. The inference engine may then pass along the conflict set to the second state, select rules. In this state, the inference engine may apply some selection strategy to determine which rules will actually be executed. The selection strategy may be hard-coded into the engine or may be specified as part of the model. Finally the selected instantiations may be passed to the third state, execute rules. The inference engine may execute, or fire, the selected rules, with the instantiation's data items as parameters. Usually the actions in the left-hand side of a rule change the data store, but they may also trigger further processing outside of the inference engine (interacting with users through a graphical user interface or calling local or remote programs, for instance). Since the data store is usually updated by firing rules, a different set of rules will match during the next cycle after these actions are performed. The inference engine may then cycle back to the first state and be ready to start over again. The inference engine stops either on a given number of cycles, or on a quiescent state of the data store when no rules match the data.

FUZZMED™ solution 2602 may have post-processing servers 2608 that have the software and hardware components to create edit, maintain the FUZZMED™ medical decision "FMD" database 106 with the up-to-date medical recommendations and decisions. FUZZMED™ Solution 2602 may then inform all FUZZMED™ Solution 2602 users with their requested information or alert them with any new medical situations.

Figure 27:
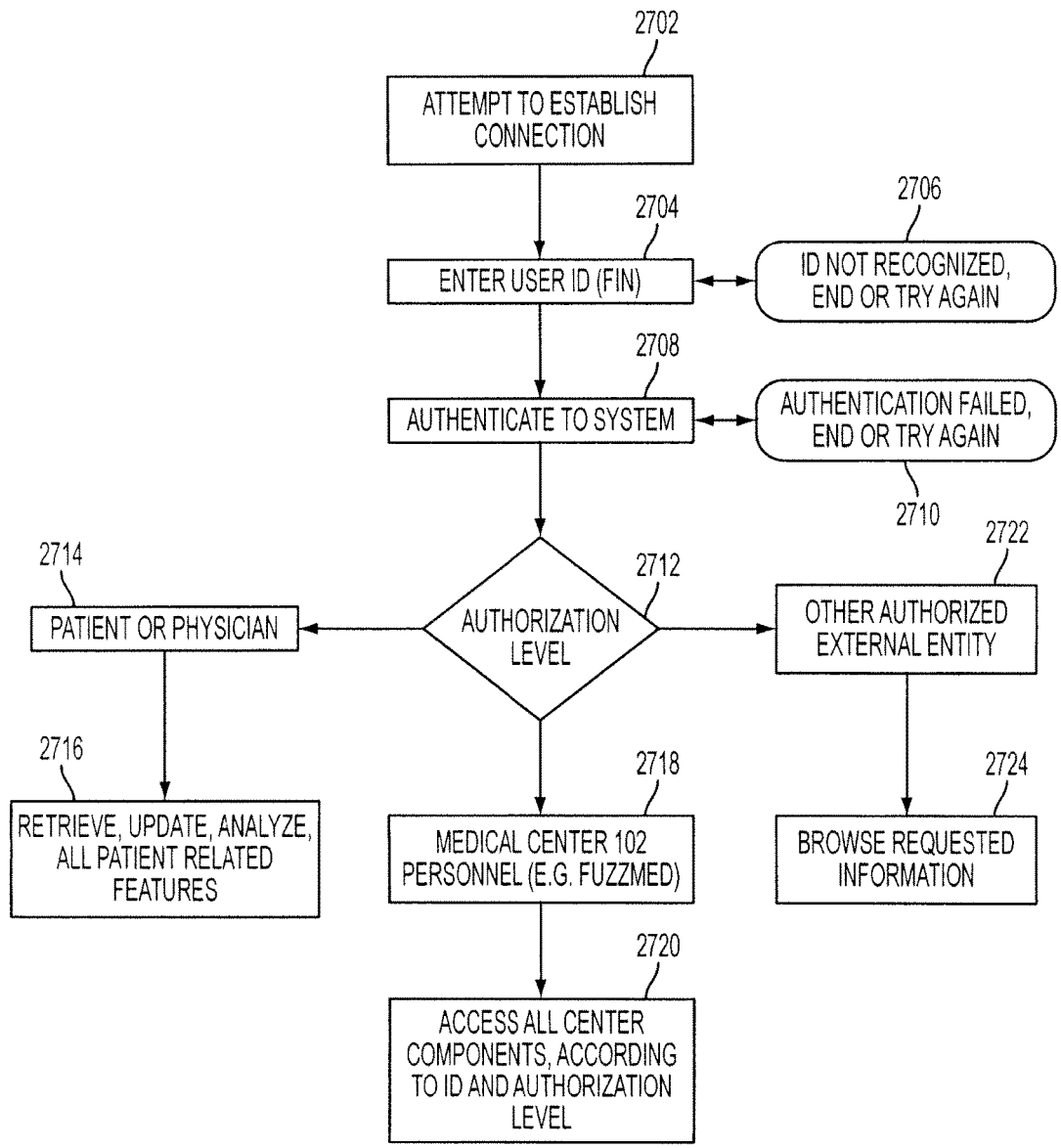
FIG. 27 depicts an exemplary flow chart of user interaction with an exemplary system according to the present invention.

FIG. 27 is a flowchart that depicts how different types of users may interact with the medical information processing center 102 or with the FUZZMED™ solution 2602. In block 2702, the user may attempt to establish a connection, for example, through a PMD 134, or through a computer, PDA, cell phone, or other device. Each user has a user identification (e.g. a FUZZMED™ Identification Number "FIN"), which he enters in block 2704. If the user ID is not recognized, the system may terminate the connection, or allow the user to try again, in block 2706.

If the user ID is recognized in 2704, then the user may be required to authenticate himself to the system in block 2708, for example, with a password, a biometric identification, or other authentication steps. If the authentication fails, the system may terminate the connection, or allow the user to try again, in block 2710.

If the authentication succeeds, an authorization level of the user (block 2712) may determine what functions of the system the user may access. A user identified as a patient or physician 2714 may retrieve, update, analyze and otherwise access all patient-related data and features, for a specific patient, in block 2716. Personnel of medical information processing center 102, e.g. administrators, programmers, etc. 2718, may access all medical information processing center 102 components, within a specific authorization levels, in block 2720. Other authorized external entities 112 (block 2722) may be able to browse or search for requested information, without making changes to the data, in block 2724.

Examples Of Embodiments In Use

The following examples are meant to illustrate various scenarios of uses for embodiments of the present invention.

First Example

A patient is started on a cholesterol lowering medication and he does well for the next two months. However he gets a blood test and his liver function tests become mildly elevated. The medical center will notify the patient, physician, pharmacist, and all related health entities, of the potential side effects of the medication and advise the patient to notify his physician. The medical center may also tell the patient that mild elevation of liver function tests are not a particular concern to the patient, especially if he has no symptoms of liver failure. The medical center may also notify a patient on a cholesterol agent to get his liver function checked if such a test is not reported on his medical record. This decision making may be in the form of an alert reminder and a suggestion to the patient, rather than a requirement, because embodiments of the invention may not be intended to replace the physician's clinical decision or direct patient care of their patients.

Second Example

Mr. John Smith is a 45 year old male with moderate obesity (body mass index 40%), hypertension, family history of heart disease, and hypercholesteremia. He has complaints regarding knee pain, increased somnolence (sleepiness), his wife complains about his snoring, he has decreased energy and libido. His medications include hydrochlorothiazide. His lab results include a fasting glucose of 110 and otherwise normal chemistries and cell blood count. His exam is consistent with a blood pressure of 160/90, swollen erythematous right joint pain, and his ECG reveals sinus with left ventricular hypertrophy. His chest x-ray shows cardiomegaly. Based on this information and any other available information in the medical center, AI derivation 124 will conclude that Mr. John Smith has gout in his right knee, sleep apnea, and erectile dysfunction. In addition, the medical center may identify several health maintenance issues. For example, Mr. Smith has a 20% chance for developing a myocardial infarction (heart attack) in the next ten years. The medical center may issue the following recommendations. Start on indomethacin (indocin) if his kidney function is normal, or colchicine if his kidney function is marginal. Follow up with further blood tests for his gout. Visit a sleep center. Loose weight. Further testing needed for his sleep apnea and erectile dysfunction.

Third Example

Mr. Smith (of the Second Example) is also now a diabetic, and his blood pressure medication is under treated. He also has erectile dysfunction, which is a marker for micro vascular disease and coexists with cardiovascular disease. The medical center may advise the physician and patient to obtain a stress test, echocardiogram, and referral to a cardiologist. To reduce his risk for having a stroke, heart attack, or death, the medical center may advise the patient and physician and any related health related domain entity to do the following. Start a cholesterol lowering medication, and aspirin. Add an ACE inhibitor. Add blood pressure medication that will lower his heart attack risk.

While the physician treating this patient may be able to come up with the same conclusion, in many cases, the physician will spend most of the time treating only the main complaint of the patient, and may not have time to address his other health maintenance problems, which have more future prognostic implications. The fact that the medical center has a suggested solution for Mr. Smith allows the physician to focus his time spent with the patient.

Fourth Example

A patient presents to a hospital emergency room, from a 911 call or Emergency Medical Service (EMS), with chest pain. The patient is admitted to the hospital and gets a stress test the next morning. The stress test is positive and the patient undergoes cardiac catheterization and stenting of his left anterior descending artery. The patient is discharged from the hospital to follow-up with his primary care doctor. The patient is a Jehovah witness, has marginal kidney function, elevated cholesterol, smokes, abnormal electrocardiogram (ECG), elevated liver function tests, and a prior workup for kidney function has been done. He is also on COUMADIN® because of a stroke he had two years ago. He also has bipolar disorder (psychiatric disorder) is non-compliant with his medications, and has advanced directives that he does not want to be resuscitated.

The medical center will acquire his information initially from the 911 EMS entity. Through the AI conduction component 118, the patient's medical information will be transmitted, along with all pertinent information such as demographics and ECG readings, to the medical center. The medical center will inform all its entities and components of the patient's demographics and medical condition, such as, vital signs, ECG and any medical information obtained on this patient from the 911 EMS. The medical center will then acquire through the AI conduction component 118, all the EMR and EHR related data to the patient's medical management from all of the external entities, such as hospitals, outpatient clinics, outpatient laboratory data, etc. The medical center will then process the information through the AI derivation component 124 and then signal possible diagnoses and suggested testing or treatments.

The medical center will now, through the AI conduction component 118, access all information from every hospital, doctor's office, urgent care center, laboratory, radiologist, and insurance health care provider data pertinent to the patient's care. If the patient had a prior ECG, which is always not available if the patient is coming to a different hospital, or prior cardiac workup such as a catheterization or stress testing, then that information is immediately updated to the medical center for processing.

The medical center, through the AI derivation component 124, will have acquired all the patient's EHR and EMR information and start to form an AI derivation regarding his care, using the standard medical guidelines database as an ancillary resource and all other pertinent parts of the health care delivery system.

Through the AI derivation component 124, the medical center in this example will know that this patient smokes, may have an allergy to iodine, has high cholesterol, and has an abnormal ECG reading. AI derivation 124 will communicate with the emergency facility to admit the patient to the emergency room (ER), check the patient's enzymes for myocardial infarction, and administer oxygen. The AI derivation will also advise the patient to get a nuclear stress test because it knows that his ECG is abnormal, and order a nuclear stress test rather than a regular stress test.

A diagnosis protocol 126 and a therapy protocol 128 may also be generated and fed into the AI derivation component 124. Diagnosis protocol 126 and therapy protocol 128 information will be provided to the cardiologist and any other related health care entity to assist in providing any needed solution.

The AI derivation will also advise the cardiologist regarding the patient's iodine allergy that the patient needs pre-medication with steroids before the patient's cardiac catheterization. The AI derivation will also be based on demographic data from the insurance health care providers and standard medical guidelines (through the AI conduction component 118), and will recommend that the patient stop smoking and takes a special kind of blood pressure medication that can prevent a heart attack such as an angiotensinogen converting enzyme inhibitor (e.g. RAMIPRIL®) as well as an anti platelet agent based on American College of Cardiology (ACC) Guidelines. The patient is also noted to have a low blood count, and since he is on the blood-thinning medication COUMADIN®, there is a potential for a bleeding source for this patient.

AI derivation will inform the patient's pharmacy that his blood count is low and that his physician should consider holding COUMADIN®, if feasible, since the patient may have a source for bleeding. In addition it will have found that his liver function tests are abnormal because he drinks and he was on a cholesterol medication. It will also advise that there is a potential reaction with his cholesterol medication.

AI derivation will also include in its analysis: that the patient is a Jehovah's witness; that his advanced directive states that he does not want resuscitation; his demographics; and insurance health providers. As a Jehovah's witness, the patient may not accept blood transfusions and hence he may not be a suitable candidate for open heart surgery especially with low blood count.

AI derivation will also know that the patient's kidney has marginal function and that only a special type of dye needs to be used in the cardiac catheterization and he needs to use certain intravenous (IV) fluids for his cardiac catheterization since his stress test is abnormal. AI derivation will also retrieve his prior kidney workup because he had abnormal kidney function from the outpatient radiology entity and hence the patient will need certain blood tests and urine tests to be done as well as nephrology consultation.

AI derivation will conclude, based on the patient's psychological profile (bipolar disorder), advanced directives, smoking history, status as a Jehovah's witness, and possible bleeding, that the patient is a better candidate for stenting than for open heart surgery. AI derivation will suggest that the patient receive a bare metal stent during his catheterization procedure rather than a drug coated stent, since smokers and patients who are non-compliant with medications may clot (close) their stents if they do not take their blood thinners. This AI derivation is based on clinical and human experiences that go beyond equation derivations.

The medical information processing center 102 will now inform each entity of pertinent AI derivation recommendations. In this patient, the cardiologist will be informed that the patient has kidney issues, and a possible allergy to iodine (e.g. in dye), so the cardiac catheterization will need to have certain 1V fluids and steroid pre-medication. The pharmacist will be alerted that the patient has elevated cholesterol and that the patient needs to substitute an alternative cholesterol medication pending a physician's review of the patient's medication list. As stated above, the pharmacy will be notified of potential bleeding with COUMADIN®.

The medical information processing center 102 will also inform and give a complete AI derivation of the patient's electronic medial and health records to his outpatient physician, informing the physician that this patient still smokes and his liver function tests are elevated with the potential reaction of his current cholesterol medication and suggest to an alternative agent. It will provide an artificially derived discharge summary of his events in the hospital. The medical information processing center 102 will also update all outpatient and inpatient (e.g. hospital radiology) centers where this patient has been in the past about the patient's iodine allergy. If the patient returns to these centers, the centers will need to provide pre-medication, as well as certain IV medications, due to the patient's marginal kidney status.

The medical information processing center 102 will also alert the physician that the patient will need follow-up with certain specialists, such as a cardiologist, a nephrologist, and a gastroenterologist for the patient's current medical problems. In addition, the primary care physician will need to know that the physician has to monitor the patient's liver function tests and kidney function more closely now that the patient needs cholesterol lowering medication and blood pressure medication that affects kidney function (e.g. angiotensinogen converting enzyme inhibitor).

The medical information processing center 102 also through AI derivation will contact the pharmacy, regulatory and non regulatory agencies such as the FDA (food and drug administration), and physicians regarding potential interactions of certain medications. This is based on AI derivation monitoring of laboratory results such as kidney and liver, cardiac monitoring such as ECG (drugs that alter the QT interval), and cell blood count.

Fifth Example

Embodiments of the present invention may be used to manage a medication clinic to observe and report the effects and interactions of a specified medication, for example, a COUMADIN® clinic. Warfarin (e.g. COUMADIN®) is an anticoagulant very frequently used in patients with cardiovascular disease, venous and arterial thromboembolism (blood clots), pulmonary thromboembolism, artificial heart valves, prior stroke, peripheral vascular disease, dialysis grafts, cardiac arrhythmias, or clots inside the heart and vascular system. Due to labor intensiveness, cost prohibitions, and low reimbursement, a COUMADIN® clinic is not taken on by many physicians. The responsibility for the follow-up of the patients carries a certain liability that in today's legal environment not many physicians are willing to take.

The systems and methods provided by embodiments of the present invention may provide an answer to a vexing problem in maintaining adequate levels of anticoagulation.

The medical center would provide a suggestion to a health professional to approve the necessary changes to the COUMADIN® dosing needed for the management of these patients on anticoagulants. Currently, COUMADIN® clinics are run mostly by physician offices and, frequently, the doses of COUMADIN® are either under- or over-dosed, and the reporting of the results are almost invariably late. In other words, the physicians and their offices are not quick to act on the results to adjust the dosing of COUMADIN®.

Embodiments of the invention can, through interaction with laboratories and pharmacies as well within its own clinic, report the lab results to the patient and the physician through the AI conduction component 118 and communication protocols.

The advantage is huge since the bleeding risk of elevated overdosed international normalized ratio (INR) is frequent and consequences dire, such as intracranial and gastrointestinal bleeding. The medical center may provide the management that most physicians find hard maintain due to staff, labor, cost, and time restraints.

COUMADIN® clinic example: Mrs. Judy Brown is on COUMADIN® for an artificial heart valve and her goal INR, which is a level of blood thinning required for patients on COUMADIN®, is 2.5-3.5. Mrs. Brown is also on a blood pressure medication diltiazem, digoxin, and her doctor started her on a new antibiotic LEVAQUIN® for an upper respiratory infection. The medical center will access, from the pharmacy, Mrs. Brown's medications, and notify the patient, pharmacy, and physician that the three medications prescribed (diltiazem, digoxin, and LEVAQUIN®) will drastically increase Mrs. Brown's INR levels and predispose her to unwarranted bleeding risk. Henceforth, the medical center will advise all related entities in the health care domain that it is best to decrease Mrs. Brown's dosage of COUMADIN® while she is taking LEVAQUIN®. This solution is drastically needed in an overtaxed health care delivery system. While the physician, pharmacy, and laboratory, are striving to achieve positive and safe outcomes for the patient, these efforts are conventionally hampered by labor, time and cost obstacles. The exemplary COUMADIN® center may reduce the labor, time, and cost associated with monitoring COUMADIN® and this would achieve patient safety and reduction of unwarranted bleeding side effect of elevated INR or thromboembolic events from excessive clotting from under-dosed INR levels.

Sixth Example

One of the most important goals of 911-EMS is to provide care to the patient as early as possible, and to triage appropriate therapy to the appropriate health care center. For example, cardiovascular disease has the largest burden on the health care in the United States with myocardial infarction (heart attack) and congestive heart failure causing a major portion of morbidity and mortality to the population. Most heart attacks and strokes do not get appropriately treated in a timely manner and that results in significant morbidity and mortality. The need to treat a patient with a heart attack and favorably affect their outcome should be less than 90 minutes (the so-called door to balloon angioplasty).

Figure 29:
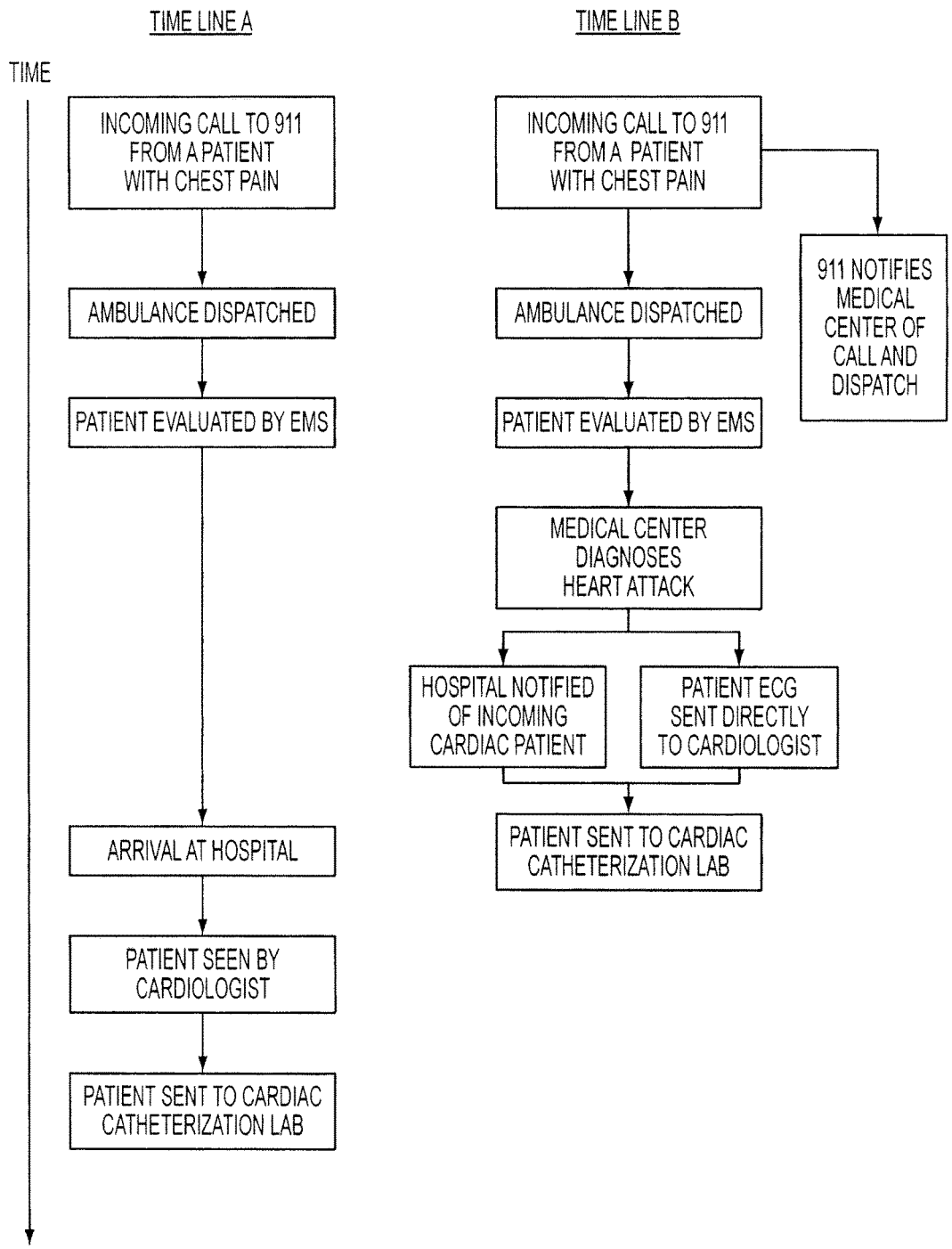
FIG. 29 depicts two exemplary time lines of a conventional emergency response and an emergency response according to embodiments of the present invention.

As seen in FIG. 29, conventionally in Time Line A, a person experiencing chest pain may call an emergency response service, such as 911. An ambulance is dispatched. The ambulance arrives, and the emergency medical technicians administer an ECG while the patient is en route to the hospital. When the patient arrives at the hospital, the patient sees a cardiologist, perhaps after waiting for the cardiologist to arrive from off-site. After evaluation from the cardiologist, the patient is finally referred for a cardiac catheterization. Conventionally, this process may take over the recommended 90 minutes from infarction to catheterization or other treatment.

In an exemplary embodiment, in Time Line B, a patient calls 911-EMS (or other emergency service) with chest pain. The 911 service may notify the medial center 102 of the potential heart attack, and about the ambulance dispatch, including to which hospital the patient will be transported. EMS arrives and carries outs an examination including checking vital signs and an ECG. The ECG data and other patient data is transmitted to medical center 102 and may also be transmitted to a cardiologist, and any information from the medical center 102 is forwarded to the emergency technicians, for example, through an AI ECG device, regarding this patient. The medical center 102, or alternatively, the AI ECG, may then generate a diagnosis that this patient is having an anterior myocardial infarction.

A diagnosis protocol will generate a diagnosis that this patient is 60 years old, has had chest pain within the time window for percutaneous intervention, no allergies to iodine, has acceptable kidney function, is physically active, has no recent strokes or gastrointestinal bleeding, is not severely demented, and has no prior cardiac disease based on any information available from the medical center or other related health care entity.

Based on the available information a therapy protocol will be generated stating that the patient is an acceptable patient for percutaneous coronary intervention "PCI". The medical center will deliver a signal to the hospital and cardiologist, and any other related health care domain, to ask for permission to proceed to the cardiac catheterization laboratory upon patient arrival. The time for this sequence may be within the recommended 90 minutes to catheterization, or less.

In an alternative embodiment of the sixth example, the patient may perform an at-home ECG, for example, with a portable ECG device, or a wearable ECG device, such as an ECG vest. The ECG device may contact both the 911 service for ambulance dispatch and the medical center 102, or may, at least, inform the patient that he should call 911.

The examples and embodiments described herein are non-limiting examples.

The invention has been disclosed in conjunction with presently preferred embodiments thereof, and a number of exemplary modifications and variations have been discussed. Other modifications and variations will readily suggest themselves to persons of ordinary skill in the art. In particular, various embodiments of medical information processing center 102 and of PMD 134 have been discussed. Various other exemplary browsing, scanning, capture, access, storage, and retrieval features have also been incorporated with various exemplary combinations. The present invention includes combinations of differently configured devices, networks, software, hardware or firmware, other than those described. The invention also may include alternative configurations with different exemplary features. For example, various alternative storage forms, types, compression methods, encryption and security features, privacy protection measures, biometric access, cryptographic controls, georeferencing, networking, communications, backup, update, or archival, etc. may be incorporated into other exemplary embodiments within the scope of the present invention. The invention is intended to embrace all such modifications and variations as fall within the spirit and broad scope of the appended claims.

The foregoing description of exemplary embodiments of the invention provides illustration and description, but is not intended to be exhaustive or to limit the invention to the precise form disclosed. Modifications and variations are possible in light of the above teachings or may be acquired from practice of the invention. For example, while a series of acts has been described with regard to FIG. 10, the order of the acts may be modified in other implementations consistent with the principles of the invention. Further, non-dependent acts may be performed in parallel.

In addition, implementations consistent with principles of the invention can be implemented using devices and configurations other than those illustrated in the figures and described in the specification without departing from the spirit of the invention. Devices or components may be added or removed from the implementations of FIGS. 1, 2, and 28 depending on specific deployments or applications. Further, disclosed implementations may not be limited to any specific combination of hardware.

Further, certain portions of the invention may be implemented as "logic" that performs one or more functions. This logic may include hardware, such as hardwired logic, an application-specific integrated circuit, a field programmable gate array, a microprocessor, software, wetware, or any combination of hardware, software, and wetware.

No element, act, or instruction used in the description of the invention should be construed as critical or essential to the invention unless explicitly described as such. Also, as used herein, the article "a" is intended to include one or more items. Where only one item is intended, the term "one" or similar language is used. Further, the phrase "based on," as used herein is intended to mean "based, at least in part, on" unless explicitly stated otherwise. Further, the conjunction "or" as used herein is intended to mean an inclusive "or", i.e. "A, B, or C" means any of the following: A; B; C; A & B; A & C; B & C; A & B & C.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

In the preceding description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still co-operate or interact with each other.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, as apparent from the following discussions, it is appreciated that throughout the specification discussions utilizing terms such as "processing," "computing," "calculating," "determining," or the like, refer to the action or processes of a computer or computing system, or similar electronic computing device, that manipulate or transform data represented as physical, such as electronic, quantities within the computing system's registers or memories into other data similarly represented as physical quantities within the computing system's memories, registers or other such information storage, transmission or display devices.

In a similar manner, the term "processor" may refer to any device or portion of a device that processes electronic data from registers or memory to transform that electronic data into other electronic data that may be stored in registers or memory. A "computing platform" may comprise one or more processors.

Embodiments of the present invention may include apparatuses for performing the operations herein. An apparatus may be specially constructed for the desired purposes, or it may comprise a general purpose device selectively activated or reconfigured by a program stored in the device.

The scope of the invention is defined by the claims and their equivalents.

What is claimed is:

1. A system, comprising:
   at least one source of medical information;
   at least one source of personal medical data for at least one patient; and
   at least one server including one or more processors, wherein the medical information and the personal medical data are accessible to the at least one server, the at least one server including
   a self-learning artificial intelligence (AI) component executed by the one or more processors, which forms derivatives and derivations of acquired information by the one or more processors modifying the acquired information by executing one or more medical analysis algorithms, performs operations including
      retrieving the personal medical data,
      converting the retrieved personal medical data to a first format including fuzzifying, which includes
         determining a plurality of fuzzy attributes for the personal medical data, where a fuzzy attribute includes determining one or more fuzzy ranges of personal medical data values that are associated with discrete values or discrete ranges of the personal medical data, where a fuzzy range represents a variable range of values that are determined by the one or more processors using self-learning AI component to incorporate acquired expert human judgement interpreting the discrete values and the discrete ranges, and defining their relationships to each other;
         determining a plurality of fuzzy categories for the plurality of fuzzy attributes, wherein the fuzzy categories each have one or more fuzzy ranges that may overlap one another,
         constructing a plurality of fuzzy functions corresponding to the plurality of fuzzy categories, wherein the plurality of fuzzy functions are constructed based on the plurality of fuzzy attributes and medical guideline data,
         determining membership values in the plurality of fuzzy categories for the plurality of fuzzy attributes based on the plurality of fuzzy functions, and
         building a plurality of fuzzy tables for each of the plurality of fuzzy attributes, and
      analyzing the converted fuzzy personal medical data together with the medical information; and identifying at least one issue requiring follow-up by the patient or by at least one external authorized entity, the AI component including
an AI conduction component for retrieving and converting the personal medical data, and
an Al derivation component for constructing the plurality of fuzzy functions based on the personal medical data and the medical information, and
at least one real-time communication link for bi-directional communication with at least one external authorized entity.

2. The system of claim 1, wherein the personal medical data for at least one patient is accessible to said at least one patient.

3. The system of claim 1, wherein the at least one server further including a data management engine to organize, store, edit, maintain, format, and process data from said personal medical data and from said medical information.

4. The system of claim 1, wherein the AI derivation component includes a diagnosis protocol; a therapy protocol; and an inference engine.

5. The system of claim 4, wherein the AI derivation component creates the diagnosis and therapy protocols using information from the at least one source of medical information.

6. The system of claim 1, wherein the at least one source of medical information includes at least one of a standard medical guideline; a pharmaceutical guideline; a government regulatory guideline; a health preventative guideline; a medical condition description; an insurance guideline; a medical journal; a research report; International Classification of Diseases (ICD) code; Current Procedural Terminology (CPT) codes; and a consensus medical committee guideline.

7. The system of claim 1, wherein the at least one source of personal medical data includes at least one of patient medical records, including physician records, vaccine records, dental records, cardiac records, pharmaceutical records, laboratory records, and radiological records; advance directives; do not resuscitate (DNR) orders; living wills; organ donation designations; scanned medical records; indexed medical information; textual medical record information; image information; streamed data; video data; audio data; handwritten notes; dictation; insurance information; prescription information; drug interaction information; allergy information; optical character recognition (OCR) data; recognized data; voice recognition data; and captured data.

8. The system of claim 1, wherein the AI component identifies at least one of a potential drug interaction; a potential side effect; a potential drug toxicity; a suggested medical test to be performed; an allergic reaction; a prior condition before a medical procedure is performed; a clinical decision; a recommendation for treatment; a recommendation for management; a recommendation for therapy; a diagnosis; and a procedure of interest to a health care monitoring agency.

9. The system of claim 1, wherein the AI component includes at least one of fuzzy logic; artificial intelligence (AI); a knowledge base (KB); a neural network; a decision support system (DSS); an agent; a software agent; and an expert system.

10. The system of claim 1, wherein the medical information and the personal medical data are accessible to the at least one server or the at least one patient for doing at least one of communicating; replicating; synchronizing; reading, writing, storing, retrieving, editing, modifying, adding to, updating, deleting, inserting, uploading, data mining, downloading, transferring, emailing, scheduling, notifying, alerting, text messaging, or instant messaging the medical information and the personal medical data.

11. The system of claim 1, wherein the at least one real-time communication link uses the Health Level 7 protocol.

12. The system of claim 1, wherein the at least one external authorized entity includes at least one of a health insurance provider, a pharmacy, a hospital, an urgent care facility, a health clinic, a physician, a physician's office, a nurse, a physician's assistant, a federal agency, a state agency, a regulatory agency, an emergency medical service, an outpatient clinic, an outpatient diagnostic clinic, a medical laboratory, the patient, and another entity authorized by said patient.

13. The system of claim 1, further comprising:
a client personal medical device, including
a storage medium for storing the personal medical data for the at least one patient; and
a communication interface for communicating with the system as one of the at least one external authorized entities.

14. The system of claim 13, further comprising:
a graphical user interface (GUI) adapted to access the personal medical data, wherein the GUI is operative on at least one of a display on the client device and a computer.

15. The system of claim 13, further comprising:
a display adapted to display at least one of the personal medical data and analyzed medical data.

16. The system according to claim 13, wherein the personal medical device includes at least one of a computing device; a communications device; a storage device including at least one of a hard drive, a universal serial bus (USB) device, a flash memory device, a memory device, a magnetic device, an optical, a magneto-optical (MO), a compact disk (CD), a radio frequency identification device (RFID), a passive device, an active device, and a chip; a card; a smartcard; a telephony device; personal digital assistant (PDA); a handheld device; a portable device; a wireless device; and a networked device.

17. The system according to claim 13, wherein the storage medium includes at least one of a hard disk; a universal serial bus (USB) storage medium; a flash memory medium; a non-volatile memory medium; memory; a magnetic medium; an optical medium; a magneto-optical (MO) medium; a compact disk (CD) medium; a digital versatile disk (DVD) medium; CD-R medium; a DVD-R medium; a radio frequency identification (RFID) medium; a passive medium; an active medium; and a medium including a chip.

18. The system of claim 13, wherein the personal medical device further includes an intelligent analysis device including at least one of means for suggesting improved care; means for suggesting improved management; means for filtering said personal medical information; means for providing a pre-operative assessment; means for providing suggestions; means for providing analyzed information comprising at least one of health, insurance or personal information; means for providing analyzed information including at least one of health insurance, civil, and government entities; means of analyzing data comprising medical conditions listed within or outside the ICD & CPT domains; means for analyzing data including at least one of genetics, hypercholesteremia, hypertension, diabetes, smoking and obesity; means of generating a medical health profile including the patient's medical conditions; means for generating a cardiovascular health profile including means for tracking at least one of patient weight, blood pressure, cholesterol profile, blood sugar level, and glycocylated hemoglobin level; means for providing a portal for medical information including means for linking at least one of healthcare provider, hospital, insurance provider, physicians, civil and government entities; means for providing organ system checkups including at least one of thyroid tests, prostate specific antigen, mammography, colonoscopy examination, pelvic exams, chest x-rays, dexa bone scan, cell blood counts, chemistries, and vaccinations; means for at least one of reducing a need for repeat testing and avoiding unnecessary testing; means for formulating a diagnosis; and means for retrieving pertinent medical data in a timely fashion.

19. The system of claim 1, further comprising:
a user interface for allowing the patient or the at least one external authorized entity to read, write, store, retrieve, edit, modify, add to, update, delete, insert, upload, data mine, download, transfer, email, schedule, notify, alert, text message, or instant message the medical information and the personal medical data.

20. The system of claim 19,
wherein the user interface includes a medical adviser component.

21. The system of claim 1, further comprising:
an electronic health record and an electronic medical record.

22. The system of claim 1, further comprising:
an alert generator for generating and sending an alert to at least one of the patient and the at least one external authorized entity regarding the identified issue.

23. A method, comprising:
receiving, by a processor, data about a patient from an external health care entity in a medical center system;
storing, by the processor, the received data in a patient medical data database (PMDB);
retrieving, by the processor, the stored patient data and converting the retrieved data to a first format in a self-learning artificial intelligence (AI) conduction component of an AI component, which forms derivatives and derivations of acquired information by modifying the acquired information by using one or more medical analysis algorithms, the converting including fuzzifying the data, which includes
determining, by the processor, a plurality of fuzzy attributes for the patient data, where a fuzzy attribute includes determining one or more fuzzy ranges of patient data values that are associated with discrete values or discrete ranges of the patient data, where a fuzzy range represents a variable range of values that are determined by using self-learning AI component to incorporate acquired expert human judgement interpreting the discrete values and the discrete ranges, and defining their relationships to each other,
determining, by the processor, a plurality of fuzzy categories for the plurality of fuzzy attributes, wherein the fuzzy categories each have one or more determined fuzzy ranges patient data values that are associated with discrete values or discrete ranges of the patient data,
constructing, by the processor, a plurality of fuzzy functions corresponding to the plurality of fuzzy categories, wherein the plurality of fuzzy functions are constructed based on the plurality of fuzzy attributes and medical guideline data,
determining, by the processor, membership values in the plurality of fuzzy categories for the plurality of fuzzy attributes based on the plurality of fuzzy functions, and
building, by the processor, a plurality of fuzzy tables for each of the plurality of fuzzy attributes; and
constructing, by the processor, the plurality of fuzzy functions using an AI derivation component of the self-learning artificial intelligence (AI) component;
intelligently analyzing, by the processor, the data according to medical information;
identifying, by the processor, at least one issue requiring follow-up by at least one external authorized entity; and
communicating, by the processor, the at least one issue to at least one external authorized entity.

24. The method of claim 23, further comprising:
pre-processing the received data in prior to storing the data in the PMDB, including at least one of synchronizing, organizing, maintaining, editing, and processing the received data.

25. The method of claim 23,
wherein the intelligently analyzing includes at least one of deriving a diagnosis protocol; deriving a therapy protocol; querying and retrieving data from at least one of standard medical guideline data, physician recommendations, and intelligent rules from medical experts; and using at least one of fuzzy logic; artificial intelligence (AI); a knowledge base (KB); a neural network; providing a decision support system (DSS); providing agent; providing software agent; and providing an expert system.

26. The method of claim 23, further comprising:
maintaining a medical decision database; and
updating the medical decision database with the identified at least one issue.

27. The method of claim 23, further comprising:
alerting at least one of the patient, a health care provider of the patient, and an external authorized entity of the identified at least one issue.

28. The method of claim 23, further comprising:
communicating the at least one issue to a plurality of external authorized entities.

29. The method of claim 28, further comprising:
for each of the plurality of external authorized entities, communicating a message regarding the at least one issue,
wherein the message is specific to the each of the plurality of external authorized entities.

30. A method, comprising:
receiving or placing, by a processor, medical data on a personal medical device;
retrieving, by the processor, the medical data and converting the retrieved data to a first format in a self-learning artificial intelligence (AI) conduction component of an AI, which forms derivatives and derivations of acquired information by modifying the acquired information by using one or more medical analysis algorithms, the converting including fuzzifying the medical data, which includes
- determining, by the processor, a plurality of fuzzy attributes for the medical data, where a fuzzy attribute includes determining one or more fuzzy ranges of medical data values that are associated with discrete values or discrete ranges of the medical data, where a fuzzy range represents a variable range of values that are determined by the processor using self-learning AI component to incorporate acquired expert human judgement interpreting the discrete values and the discrete ranges, and defining their relationships to each other,
- determining, by the processor, a plurality of fuzzy categories for the plurality of fuzzy attributes, wherein the fuzzy categories each have one or more fuzzy ranges that may overlap one another,
- constructing, by the processor, a plurality of fuzzy functions corresponding to the plurality of fuzzy categories, wherein the plurality of fuzzy functions are constructed based on the plurality of fuzzy attributes and medical guideline data,
- calculating, by the processor, membership values in the plurality of fuzzy categories for the plurality of fuzzy attributes based on the plurality of fuzzy functions, and
- building, by the processor, a plurality of fuzzy tables for each of the plurality of fuzzy attributes; and analyzing, by the processor, the medical data with the AI;
constructing, by the processor, the plurality of fuzzy functions based on the medical data and medical information using the self-learning artificial intelligence (AI) derivation component of the AI;
formatting, by the processor, the analyzed medical data according to the AI; and
storing, by the processor, the formatted medical data.

31. The method of claim 30,
wherein the receiving medical data includes at least one of scanning the medical data; imaging the medical data; capturing the medical data; accessing the medical data; displaying the medical data; processing the medical data; indexing the medical data; archiving the medical data; backing up the medical data; updating the medical data; providing the medical data; storing the medical data; capturing ECG data; capturing textual data; capturing image data; capturing streamed data; capturing video data; capturing audio data; capturing handwritten notes; capturing dictation; capturing insurance information; capturing prescription information; capturing drug interaction information; capturing allergy information; scanning optical character recognition (OCR) data; recognizing data; using voice recognition data; and capturing metadata about the medical data.

32. The method of claim 30,
wherein the medical data includes at least one of patient medical records; medical records including at least one of doctor records, vaccine records, dental records, and cardiac records; scanned medical records; indexed medical information; textual information; image information; streamed data; video data; audio data; handwritten notes; dictation; insurance information; prescription information; drug interaction information; allergy information; optical character recognition (OCR) data; recognized data; voice recognition data; and captured data.

33. The method of claim 30,
wherein the placing medical data includes at least one of storing the medical data on the personal medical information device; storing the medical data on a storage device; and placing the medical data on a storage medium.

34. The method of claim 30,
wherein the intelligence includes at least one of providing fuzzy logic; providing artificial intelligence (AI); providing a knowledge base (KB); providing a neural network; providing a decision support system (DSS); providing agent; providing software agent; and providing an expert system.

35. The method according to claim 30,
wherein the personal medical information device includes at least one of a computing device; a communications device; a storage device including at least one of a hard drive, a universal serial bus (USB) device, a flash memory device, a memory device, a magnetic device, an optical, a magneto-optical (MO), a compact disk (CD), a radio frequency identification device (RFID), a passive device, an active device, and a chip; a card; a smartcard; a telephony device; personal digital assistant (PDA); a handheld device; a portable device; a wireless device; and a networked device.

36. The method of claim 30,
wherein the storing on the storage device includes storing on at least one of a computing device; a communications device; a storage device including at least one of a hard drive, a universal serial bus (USB) device, a flash memory device, a memory device, a magnetic device, an optical, a magneto-optical (MO), a compact disk (CD), a radio frequency identification device (RFID), a passive device, an active device, and a chip; a card; a smartcard; a telephony device; personal digital assistant (PDA); a handheld device; a portable device; a wireless device; and a networked device.

37. The method of claim 30,
wherein the analyzing the medical data includes at least one of suggesting improved care; suggesting improved management; filtering the personal medical information; providing a pre-operative assessment; providing suggestions; providing analyzed information including at least one of health, insurance, and personal information; analyzing data including at least one of genetics, hypercholesteremia, hypertension, diabetes, smoking and obesity; generating a cardiovascular health profile including means for tracking at least one of patient weight, blood pressure; cholesterol profile, blood sugar level, and glycocylated hemoglobin level; providing organ system checkups including at least one of thyroid tests, prostate specific antigen, mammography, colonoscopy examination, pelvic exams, chest x-rays, dexa bone scan, cell blood counts, chemistries, and vaccinations; reducing a need for repeat testing; avoiding unnecessary testing; formulating a diagnosis; and retrieving pertinent medical data in a timely fashion.

38. A portable personal medical device, comprising:
a storage medium for storing personal medical data for a patient; and
a communication interface for communicating with a centralized intelligent health care system including a processor that executes a self-learning artificial intelligence (AI) component, which forms derivatives and derivations of acquired information by modifying the acquired information by using one or more medical analysis algorithms, for retrieving the personal medical data, converting the retrieved personal medical data to a first format including fuzzifying, which includes determining a plurality of fuzzy attributes for the personal medical data, where a fuzzy attribute includes the processor determining one or more fuzzy ranges of personal medical data values that are associated with discrete values or discrete ranges of the personal medical data, where a fuzzy range represents a variable range of values that are determined by the processor using self-learning AI component to incorporate acquired expert human judgement interpreting the discrete values and the discrete ranges, and defining their relationships to each other, determining a plurality of fuzzy categories for the plurality of fuzzy attributes, wherein the fuzzy categories each have one or more fuzzy ranges that may overlap one another, constructing a plurality of fuzzy functions corresponding to the plurality of fuzzy categories, wherein the plurality of fuzzy functions are constructed based on the plurality of fuzzy attributes and medical guideline data, calculating membership values in the plurality of fuzzy categories for the plurality of fuzzy attributes based on the plurality of fuzzy functions, and building, by the processor, a plurality of fuzzy tables for each of the plurality of fuzzy attributes; and analyzing the converted personal medical data with the medical information, and identifying at least one issue requiring follow-up by the patient or by at least one external authorized entity, the AI component including an AI conduction component for retrieving and converting the personal medical data, and an AI derivation component for constructing the plurality of fuzzy functions based on the personal medical data and the medical information.

39. The portable personal medical device of claim 38, further comprising:

a graphical user interface (GUI) adapted to access the personal medical data; wherein the GUI is operative on at least one of a display on the client device and a computer.

40. The portable personal medical device of claim 38, further comprising:

a display adapted to display at least one of the personal medical data and analyzed medical data.

41. The portable personal medical device of claim 38, wherein the personal medical device includes at least one of a computing device; a communications device; a storage device including at least one of a hard drive, a universal serial bus (USB) device, a flash memory device, a memory device, a magnetic device, an optical, a magneto-optical (MO), a compact disk (CD), a radio frequency identification device (RFID), a passive device, an active device, and a chip; a card; a smartcard; a telephony device; personal digital assistant (PDA); a handheld device; a portable device; a wireless device; and a networked device.

42. The portable personal medical device of claim 38, wherein the storage medium includes at least one of a hard disk; a universal serial bus (USB) storage medium; a flash memory medium; a non-volatile memory medium; memory; a magnetic medium; an optical medium; a magneto-optical (MO) medium; a compact disk (CD) medium; a digital versatile disk (DVD) medium; CD-R medium; a DVD-R medium; a radio frequency identification (RFID) medium; a passive medium; an active medium; and a medium comprising a chip.

43. The portable personal medical device of claim 38, wherein the personal medical device further includes an intelligent analysis device including at least one of means for suggesting improved care; means for suggesting improved management; means for filtering the personal medical information; means for providing a pre-operative assessment; means for providing suggestions; means for providing analyzed information including at least one of health, insurance, and personal information; means for providing analyzed information including at least one of health insurance, civil and government entities; means of analyzing data including medical conditions listed within or outside the ICD & CPT domains; means for analyzing data including at least one of genetics, hypercholesteremia, hypertension, diabetes, smoking and obesity; means of generating a medical health profile comprising the patient's medical conditions; means for generating a cardiovascular health profile including means for tracking at least one of patient weight, blood pressure; cholesterol profile, blood sugar level, and glycocylated hemoglobin level; means for providing a portal for medical information including means for linking at least one of healthcare provider, hospital, insurance provider, physicians, civil and government entities; means for providing organ system checkups including at least one of thyroid tests, prostate specific antigen, mammography, colonoscopy examination, pelvic exams, chest x-rays, dexa bone scan, cell blood counts, chemistries, and vaccinations; means for at least one of reducing a need for repeat testing or avoiding unnecessary testing; means for formulating a diagnosis; and means for retrieving pertinent medical data in a timely fashion.

* * * * *